United States Patent
Pelech

(10) Patent No.: US 6,856,914 B1
(45) Date of Patent: Feb. 15, 2005

(54) METHOD, APPARATUS, MEDIA AND SIGNALS FOR IDENTIFYING ASSOCIATED CELL SIGNALING PROTEINS

(75) Inventor: Steven Pelech, Vancouver (CA)

(73) Assignee: The University of British Columbia, Vancouver (CA)

( * ) Notice: Subject to any disclaimer, the term of this patent is extended or adjusted under 35 U.S.C. 154(b) by 481 days.

(21) Appl. No.: 09/715,623

(22) Filed: Nov. 17, 2000

Related U.S. Application Data
(60) Provisional application No. 60/216,357, filed on Jul. 5, 2000.

(30) Foreign Application Priority Data

Nov. 19, 1999 (CA) .............................................. 2290335
Nov. 22, 1999 (CA) .............................................. 2290204

(51) Int. Cl.[7] ............................ C12Q 1/42; C12Q 1/48; G01N 33/535; G01N 33/573
(52) U.S. Cl. .......................................... 702/19; 702/23
(58) Field of Search ..................................... 702/19, 23

(56) References Cited

PUBLICATIONS

Baron, et al., Journal of Immunological Methods, 1998, 219:23–43.
Charlton, et al., Journal of Cellular Biochemistry, 1999, 75:310–326.
Sanchez, et al., Electrophoresis, 1997, 18:638–641.
Takai–Igarashi and Kaminuma, In Silico Biology, 1999, 1:129–146.
Togashi, et al., American Journal of Physiology, 1997, 272(4 Pt. 1):L603–L607.
Turner, et al., Proc. Natl. Acad. Sci. USA, 1993, 90:5544–5548.
Kinexus Customer Information Package, Nov. 3, 2000.
Kinexus Press Release, Nov. 14, 2000.
Vancouver Sun Newspaper Article, Nov. 15, 2000.
Vancouver Province Newspaper Article, Nov. 15, 2000.

*Primary Examiner*—Michael Borin
(74) *Attorney, Agent, or Firm*—Burns, Doane, Swecker & Mathis, L.L.P.

(57) ABSTRACT

Methods, apparatus, media and signals for identifying associated cell signaling proteins are disclosed. The method involves producing and storing a comparison value for each pair of the cell signaling proteins in response to data values representing physical properties of respective cell signaling proteins. The method further involves identifying cell signaling protein pairs having comparison values satisfying a condition indicative of an association between the cell signaling proteins.

15 Claims, 19 Drawing Sheets

| KINASE | PHOS. STATE | PHYSICAL PROPERTY VALUES IN EACH MODEL SYSTEM ||||||||||
| --- | --- | --- | --- | --- | --- | --- | --- | --- | --- | --- | --- |
| | | 1 | 2 | 3 | 4 | 5 | 6 | 7 | 8 | 9 | 10 |
| A | P | 85 | 0 | 0 | 0 | 0 | 0 | 360 | 255 | 0 | 0 |
| | D | 0 | 180 | 142.5 | 160 | 100 | 95 | 0 | 0 | 200 | 90 |
| B | P | 22.5 | 0 | 0 | 0 | 0 | 0 | 85 | 75 | 0 | 0 |
| | D | 0 | 42.5 | 37.5 | 50 | 25 | 25 | 0 | 0 | 47.5 | 25 |
| C | P | 50 | 95 | 0 | 0 | 0 | 0 | 200 | 127.5 | 100 | 42.5 |
| | D | 0 | 0 | 63.75 | 100 | 47.5 | 50 | 0 | 0 | 0 | 0 |
| D | P | 190 | 400 | 0 | 0 | 0 | 0 | 800 | 600 | 300 | 200 |
| | D | 0 | 0 | 300 | 400 | 200 | 200 | 0 | 0 | 0 | 0 |
| E | P | 0 | 127.5 | 0 | 142.5 | 0 | 0 | 0 | 6.2 | 0 | 3.75 |
| | D | 67.5 | 0 | 112.5 | 0 | 75 | 75 | 225 | 6.25 | 0 | 3.75 |
| F | P | 0 | 50 | 0 | 50 | 0 | 0 | 0 | 0 | 1.3 | 0 |
| | D | 25 | 0 | 37.5 | 0 | 25 | 25 | 100 | 0 | 1.2 | 0 |
| G | P | 0 | 212.5 | 0 | 0 | 6.3 | 0 | 12.5 | 0 | 0 | 0 |
| | D | 112.5 | 0 | 187.5 | 250 | 6.2 | 0 | 12.5 | 0 | 0 | 0 |
| H | P | 0 | 100 | 0 | 0 | 0 | 0 | 14.5 | 0 | 2.5 | 1.2 |
| | D | 50 | 0 | 67.5 | 90 | 0 | 0 | 15.5 | 0 | 2.5 | 1.3 |
| I | P | 0 | 0 | 225 | 255 | 150 | 0 | 0 | 450 | 0 | 7.5 |
| | D | 0 | 0 | 0 | 0 | 0 | 150 | 540 | 0 | 0 | 7.5 |
| J | P | 0 | 18.75 | 159.4 | 250 | 125 | 0 | 0 | 318.8 | 0 | 0 |
| | D | 0 | 18.75 | 0 | 0 | 0 | 125 | 475 | 0 | 0 | 0 |
| K | P | 1.9 | 0 | 112.5 | 142.5 | 63.8 | 75 | 270 | 225 | 0 | 0 |
| | D | 1.85 | 0 | 0 | 0 | 0 | 0 | 0 | 0 | 0 | 0 |
| L | P | 0 | 0 | 75 | 100 | 45 | 50 | 200 | 142.5 | 2.6 | 2.4 |
| | D | 0 | 0 | 0 | 0 | 0 | 0 | 0 | 0 | 2.4 | 2.6 |
| M | P | 0 | 0 | 0 | 0 | 100 | 85 | 400 | 0 | 10 | 0 |
| | D | 0 | 0 | 0 | 0 | 0 | 0 | 0 | 300 | 10 | 0 |
| N | P | 2.5 | 2.5 | 0 | 0 | 25 | 25 | 100 | 0 | 0 | 0 |
| | D | 2.5 | 2.5 | 0 | 0 | 0 | 0 | 0 | 75 | 0 | 0 |
| O | P | 0 | 0 | 4.7 | 6.25 | 106.3 | 125 | 475 | 0 | 19 | 6.4 |
| | D | 0 | 0 | 4.7 | 6.25 | 0 | 0 | 0 | 318.75 | 18.5 | 6.1 |
| P | P | 0 | 0 | 0 | 0 | 150 | 142.5 | 600 | 0 | 0 | 0 |
| | D | 0 | 0 | 0 | 0 | 0 | 0 | 0 | 450 | 0 | 0 |
| Q | P | 0 | 0 | 5.625 | 0 | 0 | 0 | 0 | 8 | 100 | 42.5 |
| | D | 50 | 85 | 5.6 | 0 | 0 | 0 | 0 | 7 | 0 | 0 |
| R | P | 0 | 0 | 0 | 5 | 0 | 5 | 15 | 0 | 190 | 100 |
| | D | 100 | 200 | 0 | 5 | 0 | 5 | 15 | 0 | 0 | 0 |
| S | P | 0 | 0 | 0.95 | 0 | 1.2 | 0 | 0 | 0 | 42.5 | 22.5 |
| | D | 21.25 | 50 | 0.95 | 0 | 1.3 | 0 | 0 | 0 | 0 | 0 |
| T | P | 0 | 0 | 0 | 0 | 0 | 0 | 15 | 0 | 250 | 118.75 |
| | D | 125 | 225 | 0 | 0 | 0 | 0 | 15 | 0 | 0 | 0 |
| Erk1 | P | 0 | 0 | 0 | 0 | 0 | 0 | 0 | 0 | 0 | 0 |
| | D | 50 | 100 | 75 | 100 | 50 | 50 | 200 | 150 | 100 | 50 |

FIG. 4

TOTAL PER PROTEIN (TPP) DATA STORE ⤺ 56

| SYSTEM KINASE | 1 | 2 | 3 | 4 | 5 | 6 | 7 | 8 | 9 | 10 |
|---|---|---|---|---|---|---|---|---|---|---|
| A | 85 | 180 | 142.5 | 160 | 100 | 95 | 360 | 255 | 200 | 90 |
| B | 22.5 | 42.5 | 37.5 | 50 | 25 | 25 | 85 | 75 | 47.5 | 25 |
| C | 50 | 95 | 63.75 | 100 | 47.5 | 50 | 200 | 127.5 | 100 | 42.5 |
| D | 190 | 400 | 300 | 400 | 200 | 200 | 800 | 600 | 300 | 200 |
| E | 67.5 | 127.5 | 112.5 | 142.5 | 75 | 75 | 255 | 11.25 | 0 | 7.5 |
| F | 25 | 50 | 37.5 | 50 | 25 | 25 | 100 | 0 | 2.5 | 0 |
| G | 112.5 | 212.5 | 187.5 | 250 | 12.5 | 0 | 25 | 0 | 0 | 0 |
| H | 50 | 100 | 67.5 | 90 | 0 | 0 | 30 | 0 | 5 | 2.5 |
| I | 0 | 0 | 225 | 255 | 150 | 150 | 540 | 450 | 0 | 15 |
| J | 0 | 37.5 | 159.4 | 250 | 125 | 125 | 475 | 318.75 | 20 | 0 |
| K | 3.75 | 0 | 112.5 | 142.5 | 63.8 | 75 | 270 | 225 | 0 | 0 |
| L | 0 | 0 | 75 | 100 | 45 | 50 | 200 | 142.5 | 5 | 5 |
| M | 0 | 0 | 0 | 0 | 100 | 85 | 400 | 300 | 0 | 0 |
| N | 5 | 5 | 0 | 0 | 25 | 25 | 100 | 75 | 20 | 0 |
| O | 0 | 0 | 9.4 | 12.5 | 106.3 | 125 | 475 | 318.75 | 37.5 | 12.5 |
| P | 0 | 0 | 0 | 0 | 150 | 142.5 | 600 | 450 | 0 | 0 |
| Q | 50 | 85 | 11.25 | 10 | 0 | 0 | 0 | 15 | 100 | 42.5 |
| R | 100 | 200 | 0 | 0 | 0 | 10 | 30 | 0 | 190 | 100 |
| S | 21.25 | 50 | 1.9 | 0 | 2.5 | 0 | 0 | 0 | 42.5 | 22.5 |
| T | 125 | 225 | 0 | 0 | 0 | 0 | 30 | 0 | 250 | 118.75 |
| Erk 1 | 50 | 100 | 75 | 100 | 50 | 50 | 200 | 150 | 100 | 50 |

FIG. 6

FIRST NORMALIZED DATA STORE

| SYSTEM KINASE | 1 | 2 | 3 | 4 | 5 | 6 | 7 | 8 | 9 | 10 | MAX VALUE |
|---|---|---|---|---|---|---|---|---|---|---|---|
| A | 170 | 180 | 190 | 160 | 200 | 190 | 180 | 170 | 200 | 180 | 200 |
| B | 45 | 42.5 | 50 | 50 | 50 | 50 | 42.5 | 50 | 47.5 | 50 | 50 |
| C | 100 | 95 | 85 | 100 | 95 | 100 | 100 | 85 | 100 | 85 | 100 |
| D | 380 | 400 | 400 | 400 | 400 | 400 | 400 | 400 | 300 | 400 | 400 |
| E | 135 | 127.5 | 150 | 142.5 | 150 | 150 | 127.5 | 7.5 | 0 | 15 | 150 |
| F | 50 | 50 | 50 | 50 | 50 | 50 | 50 | 0 | 2.5 | 0 | 50 |
| G | 225 | 212.5 | 250 | 250 | 25 | 0 | 12.5 | 0 | 0 | 0 | 250 |
| H | 100 | 100 | 90 | 90 | 0 | 0 | 15 | 0 | 5 | 5 | 100 |
| I | 0 | 0 | 300 | 255 | 300 | 300 | 270 | 300 | 0 | 30 | 300 |
| J | 0 | 37.5 | 212.5 | 250 | 250 | 250 | 237.5 | 212.5 | 0 | 0 | 250 |
| K | 7.5 | 0 | 150 | 142.5 | 127.5 | 150 | 135 | 150 | 5 | 0 | 150 |
| L | 0 | 0 | 100 | 100 | 90 | 100 | 100 | 95 | 20 | 10 | 100 |
| M | 0 | 0 | 0 | 0 | 200 | 170 | 200 | 200 | 0 | 0 | 200 |
| N | 10 | 5 | 0 | 10 | 50 | 50 | 50 | 50 | 37.5 | 25 | 50 |
| O | 0 | 0 | 12.5 | 0 | 212.5 | 250 | 237.5 | 212.5 | 0 | 0 | 250 |
| P | 0 | 0 | 0 | 0 | 300 | 285 | 300 | 300 | 0 | 0 | 300 |
| Q | 0 | 0 | 15 | 0 | 0 | 0 | 0 | 0 | 100 | 85 | 100 |
| R | 100 | 85 | 0 | 10 | 0 | 20 | 15 | 10 | 190 | 200 | 200 |
| S | 200 | 200 | 2.5 | 0 | 5 | 0 | 0 | 0 | 42.5 | 45 | 50 |
| T | 42.5 | 50 | 0 | 0 | 0 | 0 | 15 | 0 | 250 | 237.5 | 250 |
| | 250 | 225 | | | | | | | | | |

SECOND NORMALIZED DATA STORE

| SYSTEM KINASE | 1 | 2 | 3 | 4 | 5 | 6 | 7 | 8 | 9 | 10 |
|---|---|---|---|---|---|---|---|---|---|---|
| A | 85 | 90 | 95 | 80 | 100 | 95 | 90 | 85 | 100 | 90 |
| B | 90 | 85 | 100 | 100 | 100 | 100 | 85 | 100 | 95 | 100 |
| C | 100 | 95 | 85 | 100 | 95 | 100 | 100 | 85 | 100 | 85 |
| D | 95 | 100 | 100 | 95 | 100 | 100 | 85 | 100 | 75 | 100 |
| E | 90 | 85 | 100 | 100 | 100 | 100 | 100 | 5 | 0 | 0 |
| F | 100 | 100 | 100 | 90 | 10 | 0 | 5 | 0 | 5 | 0 |
| G | 90 | 85 | 90 | 85 | 0 | 0 | 15 | 0 | 0 | 5 |
| H | 100 | 100 | 100 | 100 | 100 | 100 | 90 | 100 | 5 | 10 |
| I | 0 | 0 | 85 | 0 | 100 | 85 | 95 | 85 | 0 | 0 |
| J | 0 | 15 | 100 | 0 | 100 | 100 | 90 | 100 | 0 | 0 |
| K | 5 | 0 | 0 | 5 | 85 | 100 | 100 | 85 | 0 | 5 |
| L | 0 | 0 | 0 | 0 | 90 | 100 | 100 | 100 | 5 | 10 |
| M | 0 | 0 | 5 | 5 | 100 | 85 | 100 | 100 | 10 | 0 |
| N | 10 | 5 | 0 | 0 | 100 | 100 | 95 | 85 | 0 | 0 |
| O | 0 | 0 | 15 | 5 | 85 | 95 | 100 | 100 | 15 | 10 |
| P | 0 | 0 | 0 | 0 | 100 | 0 | 0 | 10 | 0 | 0 |
| Q | 100 | 85 | 5 | 0 | 0 | 10 | 7.5 | 0 | 100 | 85 |
| R | 100 | 100 | 0 | 0 | 10 | 0 | 0 | 0 | 95 | 100 |
| S | 85 | 100 | 5 | 5 | 10 | 10 | 0 | 0 | 85 | 90 |
| T | 100 | 90 | 0 | 0 | 0 | 0 | 6 | 0 | 100 | 95 |

COEXPRESSION COEFFICENTS STORE

| KINASE A | B | C | D | E | F | G | H | I | J | K | L | M | N | O | P | Q | R | S | T |
|---|---|---|---|---|---|---|---|---|---|---|---|---|---|---|---|---|---|---|---|
| A | 7.5 | 7.5 | 11 | 28.5 | 33 | 58 | 57.5 | 38 | 39 | 41.5 | 41 | 56.5 | 55.5 | 52 | 56.5 | 54.5 | 56.3 | 55.5 | 55.9 |
| B | 0 | 9 | 5.5 | 9.5 | 33 | 56.5 | 60 | 38 | 39.5 | 39 | 38.5 | 58.5 | 57 | 57.5 | 59 | 58 | 58.8 | 61 | 60.4 |
| C | | 0 | 8.5 | 31 | 29 | 57.5 | 56 | 43 | 37.5 | 43 | 39.5 | 59 | 57 | 53.5 | 59 | 55 | 56.8 | 59 | 57.4 |
| D | | | 0 | 29.5 | 27.5 | 58 | 57.5 | 38.5 | 39 | 39.5 | 37 | 57 | 55.5 | 57 | 57.5 | 62.5 | 60.3 | 61.5 | 63.9 |
| E | | | | 0 | 6.5 | 29 | 32.5 | 28.5 | 28 | 29.5 | 30 | 51.5 | 47.5 | 48 | 49.5 | 65.5 | 67.3 | 65.5 | 67.9 |
| F | | | | | 0 | 31.5 | 31 | 34 | 29.5 | 33 | 31.5 | 52 | 49 | 51.5 | 51 | 69 | 66.8 | 67 | 69.4 |
| G | | | | | | 0 | 7.5 | 57.5 | 54 | 53 | 56 | 75.5 | 74.5 | 74 | 75.5 | 40.5 | 43.8 | 39.5 | 42.1 |
| H | | | | | | | 0 | 60 | 57.5 | 58 | 59.5 | 75.5 | 76 | 73.5 | 77 | 38 | 37.8 | 38 | 38.4 |
| I | | | | | | | | 0 | 7.5 | 3 | 5.5 | 22 | 22 | 22.5 | 21 | 91 | 93.8 | 91 | 94.4 |
| J | | | | | | | | | 0 | 7.5 | 7 | 24.5 | 22.5 | 23 | 22 | 89.5 | 92.3 | 89.5 | 92.9 |
| K | | | | | | | | | | 0 | 4.5 | 24.5 | 23 | 23.5 | 23 | 91 | 93.8 | 91 | 94.4 |
| L | | | | | | | | | | | 0 | 24.5 | 24.5 | 22 | 23.5 | 91.5 | 94.3 | 91.5 | 94.9 |
| M | | | | | | | | | | | | 0 | 4 | 7.5 | 2 | 75 | 75.8 | 73 | 75.4 |
| N | | | | | | | | | | | | | 0 | 8.5 | 2 | 76 | 76.8 | 74 | 76.4 |
| O | | | | | | | | | | | | | | 0 | 7.5 | 71.5 | 72.3 | 69.5 | 72.9 |
| P | | | | | | | | | | | | | | | 0 | 77 | 77.8 | 75 | 77.4 |
| Q | | | | | | | | | | | | | | | | 0 | 8.3 | 8 | 4.6 |
| R | | | | | | | | | | | | | | | | | 0 | 7.3 | 3.7 |
| S | | | | | | | | | | | | | | | | | | 0 | 6.6 |
| T | | | | | | | | | | | | | | | | | | | 0 |

FIG. 9

COEXPRESSED PAIRS STORE

COEXPRESSED CLUSTERS STORE

STATE DATA STORE

| SYSTEM KINASE | 1 | 2 | 3 | 4 | 5 | 6 | 7 | 8 | 9 | 10 |
|---|---|---|---|---|---|---|---|---|---|---|
| A | P | D | D | D | D | D | P | P | D | D |
| B | P | D | D | D | D | D | P | P | D | D |
| C | P | P | D | D | D | D | P | P | P | P |
| D | P | P | D | P | D | D | P | P | P | P |
| E | D | P | D | D | D | D | D | N.S. | N.S. | N.S. |
| F | D | P | D | P | N.S. | N.S. | N.S. | N.S. | N.S. | N.S. |
| G | N.S. | P | P | P | P | D | D | P | N.S. | N.S. |
| H | N.S. | P | P | P | P | P | D | P | N.S. | N.S. |
| I | N.S. | P | P | P | P | P | P | P | N.S. | N.S. |
| J | N.S. | N.S. | N.S. | N.S. | P | P | P | P | N.S. | N.S. |
| K | N.S. | N.S. | N.S. | N.S. | P | P | P | D | N.S. | N.S. |
| L | N.S. | N.S. | N.S. | N.S. | P | P | P | D | N.S. | N.S. |
| M | N.S. | N.S. | N.S. | N.S. | N.S. | N.S. | N.S. | D | N.S. | N.S. |
| N | N.S. | N.S. | N.S. | N.S. | N.S. | N.S. | N.S. | N.S. | N.S. | N.S. |
| O | N.S. | N.S. | N.S. | N.S. | N.S. | N.S. | N.S. | N.S. | N.S. | N.S. |
| P | N.S. | N.S. | N.S. | N.S. | N.S. | N.S. | N.S. | N.S. | N.S. | N.S. |
| Q | D | D | N.S. | N.S. | N.S. | N.S. | N.S. | N.S. | P | P |
| R | D | D | N.S. | N.S. | N.S. | N.S. | N.S. | N.S. | P | P |
| S | D | D | N.S. | N.S. | N.S. | N.S. | N.S. | N.S. | P | P |
| T | D | D | N.S. | N.S. | N.S. | N.S. | N.S. | N.S. | P | P |

FIG. 14

COREGULATION COEFFICIENTS STORE

| KINASE | A | B | C | D | E | F | G | H | I | J | K | L | M | N | O | P | Q | R | S | T |
|---|---|---|---|---|---|---|---|---|---|---|---|---|---|---|---|---|---|---|---|---|
| A | 0 | 1.6 | 0.4 | 0.4 | 0 | 0 | 0 | 0 | 0 | 0 | 0 | 0 | 0 | 0 | 0 | 0 | 0 | 0 | 0 | 0 |
| B |   | 0 | 0.4 | 0.4 | 0 | 0 | 0 | 0 | 0 | 0 | 0 | 0 | 0 | 0 | 0 | 0 | 0 | 0 | 0 | 0 |
| C |   |   | 0 | 2.2 | 0 | 0 | 0.5 | 0.5 | 0 | 0 | 0 | 0 | 0 | 0 | 0 | 0 | 0 | 0 | 0 | 0 |
| D |   |   |   | 0 | 0 | 0 | 0.5 | 0.5 | 0 | 0 | 0 | 0 | 0 | 0 | 0 | 0 | 0 | 0 | 0 | 0 |
| E |   |   |   |   | 0 | 1.57 | 0.5 | 0.5 | 0 | 0 | 0 | 0 | 0 | 0 | 0 | 0 | 0 | 0 | 0 | 0 |
| F |   |   |   |   |   | 0 | 0.5 | 0.5 | 0 | 0 | 0 | 0 | 0 | 0 | 0 | 0 | 0 | 0 | 0 | 0 |
| G |   |   |   |   |   |   | 0 | 1.5 | 0 | 0 | 0 | 0 | 0 | 0 | 0 | 0 | 0 | 0 | 0 | 0 |
| H |   |   |   |   |   |   |   | 0 | 0 | 0 | 0 | 0 | 0 | 0 | 0 | 0 | 0 | 0 | 0 | 0 |
| I |   |   |   |   |   |   |   |   | 0 | 2.33 | 1.0 | 1.0 | 0 | 0 | 0 | 0 | 0 | 0 | 0 | 0 |
| J |   |   |   |   |   |   |   |   |   | 0 | 1.0 | 1.0 | 0 | 0 | 0 | 0 | 0 | 0 | 0 | 0 |
| K |   |   |   |   |   |   |   |   |   |   | 0 | 3.0 | 1.5 | 1.5 | 1.5 | 1.5 | 0 | 0 | 0 | 0 |
| L |   |   |   |   |   |   |   |   |   |   |   | 0 | 1.5 | 1.5 | 1.5 | 1.5 | 0 | 0 | 0 | 0 |
| M |   |   |   |   |   |   |   |   |   |   |   |   | 0 | 2.5 | 2.5 | 2.5 | 0 | 0 | 0 | 0 |
| N |   |   |   |   |   |   |   |   |   |   |   |   |   | 0 | 2.5 | 2.5 | 0 | 0 | 0 | 0 |
| O |   |   |   |   |   |   |   |   |   |   |   |   |   |   | 0 | 2.5 | 0 | 0 | 0 | 0 |
| P |   |   |   |   |   |   |   |   |   |   |   |   |   |   |   | 0 | 0 | 0 | 0 | 0 |
| Q |   |   |   |   |   |   |   |   |   |   |   |   |   |   |   |   | 0 | 2.0 | 2.0 | 2.0 |
| R |   |   |   |   |   |   |   |   |   |   |   |   |   |   |   |   |   | 0 | 2.0 | 2.0 |
| S |   |   |   |   |   |   |   |   |   |   |   |   |   |   |   |   |   |   | 0 | 2.0 |
| T |   |   |   |   |   |   |   |   |   |   |   |   |   |   |   |   |   |   |   | 0 |

FIG. 15

COREGULATED PAIRS

COREGULATED CLUSTERS

LINKAGE COEFFICIENTS STORE

| KINASE | A | B | C | D | E | F | G | H | I | J | K | L | M | N | O | P | Q | R | S | T |
|---|---|---|---|---|---|---|---|---|---|---|---|---|---|---|---|---|---|---|---|---|
| A | 0 | 21.3 | 5.3 | 3.6 | 0 | 0 | 0 | 0 | 0 | 0 | 0 | 0 | 0 | 0 | 0 | 0 | 0 | 0 | 0 | 0 |
| B | 0 | 0 | 4.4 | 7.3 | 0 | 0 | 0 | 0 | 0 | 0 | 0 | 0 | 0 | 0 | 0 | 0 | 0 | 0 | 0 | 0 |
| C | 0 | 0 | 0 | 25.9 | 0 | 0 | 0 | 0 | 0 | 0 | 0 | 0 | 0 | 0 | 0 | 0 | 0 | 0 | 0 | 0 |
| D | 0 | 0 | 0 | 0 | 0 | 0 | 0 | 0 | 0 | 0 | 0 | 0 | 0 | 0 | 0 | 0 | 0 | 0 | 0 | 0 |
| E | 0 | 0 | 0 | 0 | 0 | 24.2 | 0 | 0 | 0 | 0 | 0 | 0 | 0 | 0 | 0 | 0 | 0 | 0 | 0 | 0 |
| F | 0 | 0 | 0 | 0 | 0 | 0 | 0.9 | 0.9 | 0 | 0 | 0 | 0 | 0 | 0 | 0 | 0 | 0 | 0 | 0 | 0 |
| G | 0 | 0 | 0 | 0 | 0 | 0 | 0.9 | 0.9 | 0 | 0 | 0 | 0 | 0 | 0 | 0 | 0 | 0 | 0 | 0 | 0 |
| H | 0 | 0 | 0 | 0 | 0 | 0 | 1.7 | 1.5 | 0 | 0 | 0 | 0 | 0 | 0 | 0 | 0 | 0 | 0 | 0 | 0 |
| I | 0 | 0 | 0 | 0 | 0 | 0 | 1.6 | 1.6 | 0 | 0 | 0 | 0 | 0 | 0 | 0 | 0 | 0 | 0 | 0 | 0 |
| J | 0 | 0 | 0 | 0 | 0 | 0 | 0 | 20 | 0 | 0 | 0 | 0 | 0 | 0 | 0 | 0 | 0 | 0 | 0 | 0 |
| K | 0 | 0 | 0 | 0 | 0 | 0 | 0 | 0 | 0 | 31.1 | 33.3 | 18.2 | 0 | 0 | 0 | 0 | 0 | 0 | 0 | 0 |
| L | 0 | 0 | 0 | 0 | 0 | 0 | 0 | 0 | 0 | 0 | 13.3 | 14.3 | 0 | 0 | 0 | 0 | 0 | 0 | 0 | 0 |
| M | 0 | 0 | 0 | 0 | 0 | 0 | 0 | 0 | 0 | 0 | 0 | 66.7 | 0 | 0 | 0 | 0 | 0 | 0 | 0 | 0 |
| N | 0 | 0 | 0 | 0 | 0 | 0 | 0 | 0 | 0 | 0 | 0 | 0 | 6.1 | 6.5 | 6.4 | 6.5 | 0 | 0 | 0 | 0 |
| O | 0 | 0 | 0 | 0 | 0 | 0 | 0 | 0 | 0 | 0 | 0 | 0 | 6.1 | 6.1 | 6.8 | 6.4 | 0 | 0 | 0 | 0 |
| P | 0 | 0 | 0 | 0 | 0 | 0 | 0 | 0 | 0 | 0 | 0 | 0 | 0 | 62.5 | 33.3 | 125 | 0 | 0 | 0 | 0 |
| Q | 0 | 0 | 0 | 0 | 0 | 0 | 0 | 0 | 0 | 0 | 0 | 0 | 0 | 0 | 29.4 | 125 | 0 | 0 | 0 | 0 |
| R | 0 | 0 | 0 | 0 | 0 | 0 | 0 | 0 | 0 | 0 | 0 | 0 | 0 | 0 | 0 | 33.3 | 0 | 24.1 | 25 | 43.5 |
| S | 0 | 0 | 0 | 0 | 0 | 0 | 0 | 0 | 0 | 0 | 0 | 0 | 0 | 0 | 0 | 0 | 0 | 0 | 27.4 | 54.1 |
| T | 0 | 0 | 0 | 0 | 0 | 0 | 0 | 0 | 0 | 0 | 0 | 0 | 0 | 0 | 0 | 0 | 0 | 0 | 0 | 30.3 |

| PAIR NUMBER | LINKAGE COEFFICIENT | KINASE PAIR |
|---|---|---|
| 1 | 125 | M, P |
| 2 | 125 | N, P |
| 3 | 66.7 | K, L |
| 4 | 62.5 | M, N |
| 5 | 54.1 | R, T |
| 6 | 43.5 | Q, T |
| 7 | 33.3 | I, K |
| 8 | 33.3 | M, O |
| 9 | 33.3 | O, P |
| 10 | 31.1 | I, J |
| 11 | 30.3 | S, T |
| 12 | 29.4 | N, O |
| 13 | 27.4 | R, S |
| 14 | 25.9 | C, D |
| 15 | 25 | Q, S |
| 16 | 24.2 | E, F |
| 17 | 24.1 | Q, R |
| 18 | 21.3 | A, B |
| 19 | 20 | G, H |
| 20 | 18.2 | I, L |
| 21 | 14.3 | J, L |
| 22 | 13.3 | J, K |
| 23 | 7.3 | B, D |
| 24 | 6.8 | L, O |
| 25 | 6.5 | K, N |
| 26 | 6.5 | K, P |
| 27 | 6.4 | K, O |
| 28 | 6.4 | L, P |
| 29 | 6.1 | K, M |
| 30 | 6.1 | L, M |
| 31 | 6.1 | L, N |
| 32 | 5.3 | A, C |
| 33 | 4.4 | B, C |
| 34 | 3.6 | A, D |
| 35 | 1.7 | E, G |
| 36 | 1.6 | F, G |
| 37 | 1.6 | F, H |
| 38 | 1.5 | E, H |
| 39 | 0.9 | C, G |
| 40 | 0.9 | C, H |
| 41 | 0.9 | D, G |
| 42 | 0.9 | D, H |

METHOD, APPARATUS, MEDIA AND SIGNALS FOR IDENTIFYING ASSOCIATED CELL SIGNALING PROTEINS

This application claims priority under 35 U.S.C. §§ 119 and/or 365 to Application No. 2,290,335 filed in Canada on Nov. 19, 1999; Application No. 2,290,204, filed in Canada on Nov. 22, 1999, and U.S. Provisional Application Ser. No. 60/216,357, filed on Jul. 5, 2000; the entire content of which is hereby incorporated by reference.

FIELD OF THE INVENTION

The present invention relates to analysis of biological information, and more particularly, to methods, apparatus, media and signals for identifying associated cell signaling proteins.

BACKGROUND OF THE INVENTION

Within a biological cell, levels of expression and activity of proteins are regulated by a subset of typically about 10% of the proteins, the subset that is dedicated to cell communications and control. This subset is referred to herein as "cell signaling proteins". One of the largest classes of such cell signaling proteins is a class of enzymes called protein kinases. Protein kinases control other proteins by catalyzing their phosphorylation, a process that is reversible by protein phosphatases. Virtually all cell signaling proteins are either protein kinases or regulators of protein kinases or their substrates. Protein kinases often operate within signaling pathways that are further integrated into signaling networks.

Generally, such signaling pathways and networks govern and coordinate all cellular functions, including cell structure, metabolism, reproduction, adaptation, differentiation and death, for example.

Moreover, protein kinases appear to be disproportionately linked to cell diseases. For example, approximately half of the hundred or so identified cancer-inducing genes, or "oncogenes", encode protein kinases, and the remaining half appear to encode proteins that either activate kinases or are phosphorylated by kinases. In addition, over 400 human diseases, such as cardiovascular disease, diabetes, arthritis and other immune disorders, and Alzheimer's disease and other neurological disorders, for example, have been linked to defective signaling through protein kinases.

If protein kinases and their respective signaling pathways and networks can be identified and understood, then monitoring of the kinases could feasibly be used to obtain a molecular diagnosis of a disease condition. In addition, if a particular problematic protein kinase in a diseased cell can be identified, it may be possible to inhibit either the problematic kinase or its downstream effectors, to effectively block the improper proliferative signaling, or even to initiate apototic processes leading to programmed death of the diseased cells such as tumor cells for example.

Therefore, it is particularly important to identify not only the protein kinases and other cell signaling proteins themselves, but more importantly, the signaling pathways and networks in which they operate.

Identification of the kinases themselves is presently being achieved through various genome sequencing projects, and virtually all of the human kinases are expected to be identified within the next year.

However, existing techniques are not suitable for identifying signaling pathways and networks of cell signaling proteins. Most protein kinases appear to be activated as a consequence of either their own phosphorylation by upstream kinases, or by autophosphorylation (i.e. self-phosphorylation), however, nucleic acid-based techniques such as those used for detection of gene expression cannot be used to monitor post-translational events such as phosphorylation.

Conversely, conventional measurement techniques that are capable of differentiating between phosphorylated and dephosphorylated states of proteins, such as the standard two-dimensional sodium dodecyl sulphate polyacrylamide gel electrophoresis (SDS-PAGE) technique of Dr. Patrick O'Farrell for example, have experienced great difficulty in detecting protein kinases, which are typically present at very minute levels in a cell compared to other proteins. For example, public databases exist containing identifications of over a thousand different proteins on two-dimensional gel maps, but containing identifications of scarcely more than a dozen of the estimated two thousand or so protein kinases that are thought to be encoded by the human genome.

Recent modifications of the two dimensional SDS-PAGE technique involving the Western blotting procedure followed by detection using a single monoclonal anti-kinase antibody per blot, for example, have been attempted. However, the recovery of most protein kinases from the first dimension gel is typically less than 10%, with the result that 90% or more of protein kinases do not enter the second dimension gel and are therefore unresolved. Accordingly, these recent modified techniques are typically able to detect only four or five of the several hundred protein kinases that are expected to be present in a given cell.

Due to the above difficulties in obtaining measurements of levels and phosphorylation states of cell signaling proteins such as kinases, few, if any, analytical techniques exist for the analysis of kinase measurements to yield information about the signaling pathways and networks in which the kinases operate.

However, the inventor of the invention disclosed and claimed herein has recently invented a new and useful method for detection of multiple cell signaling proteins, such as multiple kinases or multiple kinase substrates (i.e. proteins that are phosphorylated by kinases), whereby the presence and phosphorylation states of a large number of kinases and/or kinase substrates may be measured in a single sample.

Thus, with the advent of this new experimental measurement technique, there is a need for new analytical techniques for analyzing cell signaling protein measurements, to identify particular cell signaling proteins that are associated with one another in common signaling pathways.

SUMMARY OF THE INVENTION

The present invention addresses the above need by providing a method and an apparatus for identifying associated cell signaling proteins. The method involves producing and storing a comparison value for each pair of the cell signaling proteins in response to data values representing physical properties of respective cell signaling proteins. The method further involves identifying cell signaling protein pairs having comparison values satisfying a condition indicative of an association between the cell signaling proteins. The apparatus includes a receiver operable to receive the data values representing the physical properties of the respective cell signaling proteins, and a processor circuit in communication with the receiver. The processor circuit is configured to produce and store, in a memory, each of the comparison values, and to identify the cell signaling protein pairs having comparison values satisfying a condition indicative of an association between the cell signaling proteins.

Thus, the present invention provides a useful, concrete and tangible result, as the identification of cell signaling protein pairs satisfying a condition indicative of an association between the cell signaling proteins indicates a likelihood that such cell signaling proteins form part of a common signaling pathway.

The apparatus preferably includes memory, which is preferably a random access memory. The processor circuit is preferably configured to normalize the data values relative to at least one reference value, prior to producing the comparison values.

The processor circuit may be configured to produce a list of pairs of associated cell signaling proteins, and/or to produce a list of clusters of associated cell signaling proteins. The processor circuit may be configured to identify such a cluster of associated cell signaling proteins, the cluster including a group of the pairs of associated cell signaling proteins for which each member of each pair is present in at least one other pair of the group. More particularly, the processor circuit may be configured to identify the cluster by: generating a cluster list associated with a first cell signaling protein pair, the cluster list including an identification of the first cell signaling protein pair; adding, to the cluster list, an identification of each of the pairs that includes at least one cell signaling protein already present in the cluster list; repeating the adding following each adding of pairs to the cluster list, to effectively add to the cluster list each of the pairs that includes at least one cell signaling protein present in at least one pair added to the cluster list; eliminating, from the cluster list, each of the pairs that includes at least one cell signaling protein not found in at least one other pair in the cluster list; and repeating the eliminating following each elimination of pairs, to effectively eliminate from the cluster list each of the pairs that includes at least one cell signaling protein not present in at least one other non-eliminated pair in the cluster list.

Preferably, the receiver is operable to receive sets of cell signaling protein data, each set including the data values, the data values representing amounts of respective corresponding cell signaling proteins in biological material corresponding to the set.

If so, then the processor circuit is preferably configured to produce, as the comparison values, a coexpression coefficient for each pair of the cell signaling proteins, each coexpression coefficient representing a degree of coexpression of one cell signaling protein of the pair and the other cell signaling protein of the pair. More particularly, the processor circuit may be configured to produce each coexpression coefficient by, for each set, calculating a difference value equal to an absolute value of a difference between the data value corresponding to the one cell signaling protein and the data value corresponding to the other cell signaling protein, and adding the difference values for each of the sets to produce a sum of difference values. The processor circuit may be further configured to divide the sum by the number of the sets to produce the coexpression coefficient corresponding to the one cell signaling protein and the other cell signaling protein.

Preferably, the processor circuit is configured to identify the cell signaling protein pairs by identifying each cell signaling protein pair having a coexpression coefficient less than or equal to a threshold coexpression value. In this regard, the processor circuit is preferably configured to produce a list of coexpressed cell signaling protein pairs, the list including an identification of each cell signaling protein pair having a coexpression coefficient less than or equal to the threshold coexpression value. The processor circuit may also be configured to produce a list of clusters of coexpressed cell signaling protein pairs, each cluster including a group of the pairs of coexpressed cell signaling proteins for which each member of each pair is present in at least one other pair of the group.

The receiver is also preferably operable to receive sets of cell signaling protein data, each set including the data values, the data values indicating phosphorylation states of respective cell signaling proteins in biological material corresponding to the set. If so, then the processor circuit is preferably configured to produce, as the comparison values, a coregulation coefficient for each pair of the cell signaling proteins, each coregulation coefficient representing a degree of coregulation of one cell signaling protein of the pair and the other cell signaling protein of the pair. The processor circuit may be configured to produce each coregulation coefficient by, for each set, assigning a pair state value as a function of phosphorylation states of the one cell signaling protein and the other cell signaling protein, and adding the pair state values for each of the sets to produce a sum of pair state values. The processor circuit may be further configured to divide the sum by the number of the sets to produce the coregulation coefficient corresponding to the one cell signaling protein and the other cell signaling protein. The processor circuit is preferably configured to assign the pair state value by: assigning a first pair state value when the one cell signaling protein and the other cell signaling protein are both in a phosphorylated state; assigning a second pair state value when the one cell signaling protein and the other cell signaling protein are both in a dephosphorylated state, the second pair state value being less than the first pair state value; and assigning a third pair state value when the one cell signaling protein and the other cell signaling protein are in different phosphorylation states, the third pair state value being less than the second pair state value.

Preferably, the processor circuit is configured to identify the cell signaling protein pairs by identifying each cell signaling protein pair having a coregulation coefficient greater than a threshold coregulation value. In this regard, the processor circuit may be configured to produce a list of coregulated cell signaling protein pairs, the list including an identification of each cell signaling protein pair having a coregulation coefficient greater than the threshold coregulation value. In addition, the processor circuit is preferably configured to produce a list of clusters of coregulated cell signaling protein pairs, each cluster including a group of the coregulated cell signaling protein pairs for which each member of each pair is present in at least one other pair of the group.

The processor circuit is preferably configured to produce, as the comparison values, a linkage coefficient for each pair of the cell signaling proteins, as a function of a coexpression coefficient representing a degree of coexpression of one cell signaling protein of the pair and the other cell signaling protein of the pair, and of a coregulation coefficient representing a degree of coregulation of the one cell signaling protein of the pair and the other cell signaling protein of the pair, each linkage coefficient representing a degree of association between the one cell signaling protein and the other cell signaling protein. More particularly, the processor circuit is preferably configured to produce each linkage coefficient by, for each pair, dividing the coregulation coefficient by the coexpression coefficient.

The processor circuit is preferably further configured to produce a list of linked cell signaling protein pairs, the list including an identification of each cell signaling protein pair having a linkage coefficient greater than or equal to a threshold linkage value.

In addition, the processor circuit is preferably configured to associate at least some of the cell signaling proteins with respective common signaling pathways, in response to the linkage coefficients. The processor circuit may be configured to achieve this by identifying a group of the cell signaling proteins for which each linkage coefficient linking each cell signaling protein to each other cell signaling protein of the group is greater than or equal to a threshold linkage value. More particularly, the processor circuit may be configured to identify such a group by: generating a linkage list including a first cell signaling protein; adding, to the linkage list, each other cell signaling protein for which the linkage coefficient for the first cell signaling protein and the other cell signaling protein is greater than or equal to the threshold linkage value; and eliminating, from the linkage list, each cell signaling protein on the linkage list for which the linkage coefficient for that cell signaling protein and at least one other cell signaling protein on the linkage list is less than the threshold linkage value.

The processor circuit is preferably configured to produce lists of the common signaling pathways.

Optionally, the apparatus may further include a measuring device operable to produce the data values representing the physical properties of the respective cell signaling proteins. The measuring device may include a chemiluminescence imager operable to produce signals representative of proteins in a single dimension in an electrophoresis gel. The measuring device may further include an electrophoresis apparatus, such as a one-dimensional sodium dodecyl sulphate polyacrylamide gel electrophoresis (SDS-PAGE) measuring system for example, operable to produce the electrophoresis gel.

In accordance with another aspect of the invention, there is provided a computer readable medium for providing instructions for directing a programmable device to receive data values representing physical properties of respective cell signaling proteins, to produce and store a comparison value for each pair of the cell signaling proteins in response to the data values, and to identify cell signaling protein pairs having comparison values satisfying a condition indicative of an association between the cell signaling proteins.

In accordance with yet another aspect of the invention, there is provided a computer data signal embodied in a carrier wave. The signal includes a first code segment for directing a programmable device to receive data values representing physical properties of respective cell signaling proteins, a second code segment for directing the programmable device to produce and store a comparison value for each pair of the cell signaling proteins in response to the data values, and a third code segment for directing the programmable device to identify cell signaling protein pairs having comparison values satisfying a condition indicative of an association between the cell signaling proteins.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention,

FIG. 4 is a tabular representation of an input data values store defined in a memory shown in FIG. 2;

FIG. 6 is a tabular representation of a total per protein data store defined in the memory shown in FIG. 2;

FIG. 7 is a tabular representation of a first normalized data store defined in the memory shown in FIG. 2;

FIG. 8 is a tabular representation of a second normalized data store defined in the memory shown in FIG. 2;

FIG. 9 is a tabular representation of a coexpression coefficients store defined in the memory shown in FIG. 2;

FIG. 10 is a schematic representation of a coexpressed pairs store defined in the memory shown in FIG. 2;

FIG. 11 is a schematic representation of a coexpressed clusters store defined in the memory shown in FIG. 2;

FIG. 14 is a tabular representation of a state data store defined in the memory shown in FIG. 2;

FIG. 15 is a tabular representation of a coregulation coefficients store defined in the memory shown in FIG. 2;

FIG. 16 is a schematic representation of a coregulated pairs store defined in the memory shown in FIG. 2;

FIG. 17 is a schematic representation of a coregulated clusters store defined in the memory shown in FIG. 2;

FIG. 19 is a tabular representation of a linkage coefficients store defined in the memory shown in FIG. 2;

FIG. 20 is a tabular representation of a linkage-sorted pairs store defined in the memory shown in FIG. 2; and FIG. 21 is a schematic representation of a linked pathway groups store defined in the memory shown in FIG. 2.

DETAILED DESCRIPTION

Figure 1:
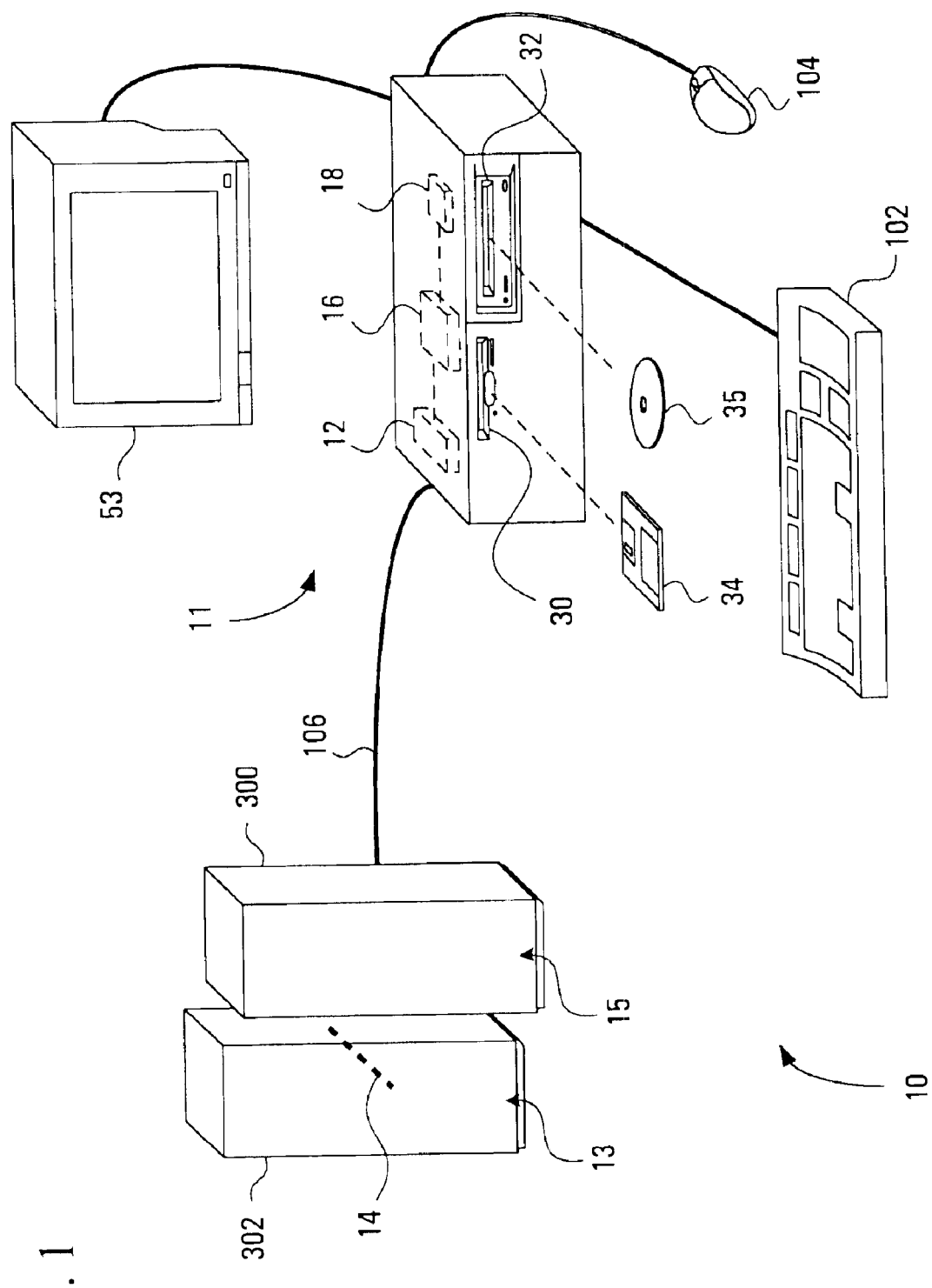
FIG. 1 is a perspective view of a system for identifying associated cell signaling proteins, according to a first embodiment of the invention.

Referring to FIG. 1, a system and an apparatus for identifying associated cell signaling proteins according to a first embodiment of the invention are shown generally at 10 and 11, respectively. In this embodiment, the apparatus includes a receiver shown generally at 12, operable to receive data values representing physical properties of respective cell signaling proteins 14. The apparatus further includes a processor circuit shown generally at 16 in communication with the receiver 12. The processor circuit 16 is configured to produce and store, in a memory 18, a comparison value for each pair of the cell signaling proteins 14 in response to the data values, and to identify cell signaling protein pairs having comparison values satisfying a condition indicative of an association between the cell signaling proteins.

In this specification, including the claims, "cell signaling proteins" means proteins that relay information within cells. Relaying information can include activities such as the binding of an extra-cellular mediator (such as a hormone, growth factor or cytokine for example) to a cell surface receptor, and the cascade of events that mediate the action of that extra-cellular mediator throughout the cell. Examples of cell signaling proteins include receptors, G proteins, second-messenger generating enzymes (such as cyclases, phospholipases and phosphodiesterases), adapter proteins, kinases, phosphatases, apoptosis proteins, heat shock proteins, transcription factors, cyclins, regulatory inhibitors, regulatory activators and scaffolding proteins.

For illustrative purposes, the remainder of this specification describes production and analysis of data representing physical properties of protein kinases. However, one of ordinary skill in the art, upon being presented with this specification, would appreciate that the embodiments of the invention described herein are equally applicable to detection and analysis of other types of cell signaling proteins.

Processor Circuit

Figure 2:
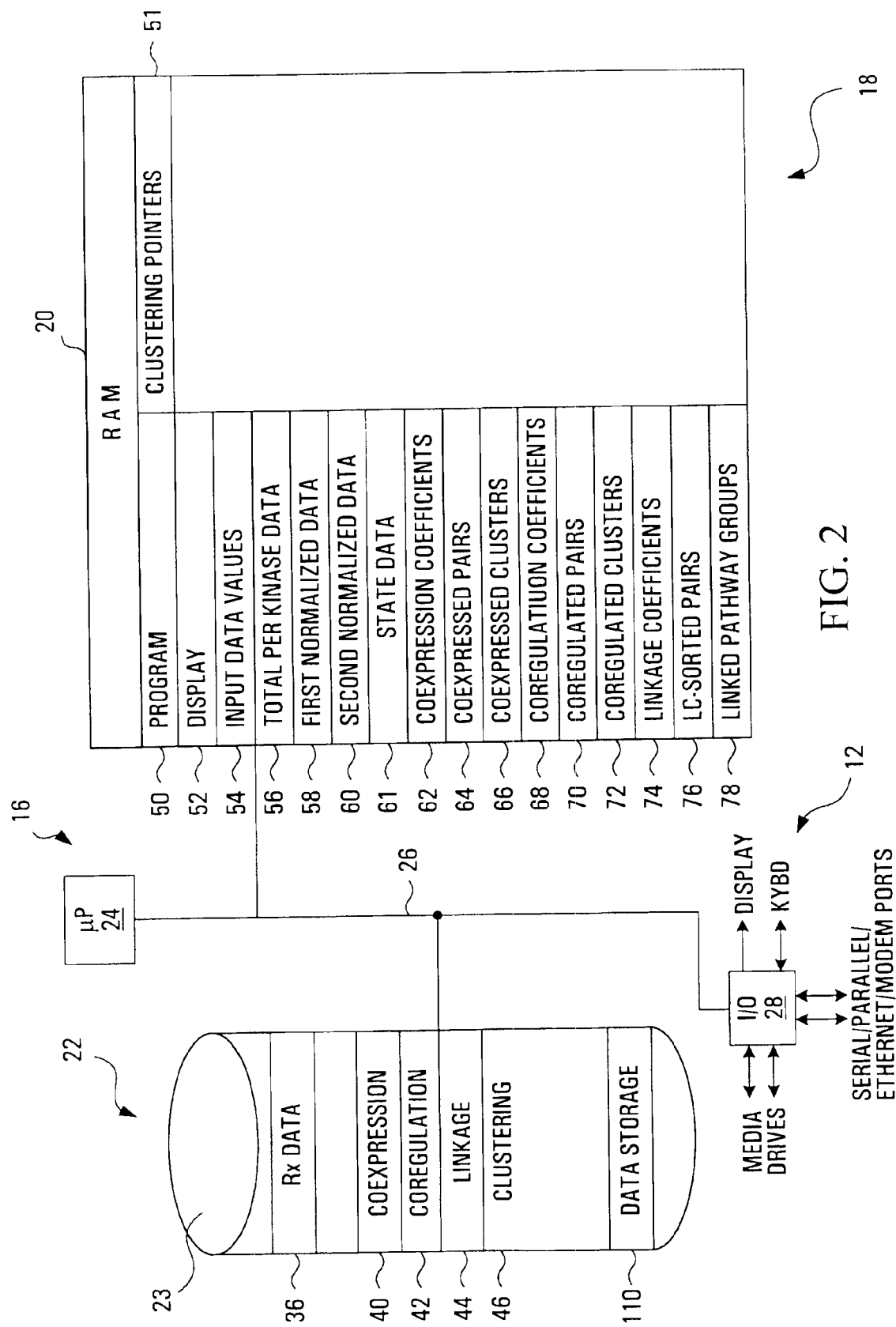
FIG. 2 is a block diagram of a processor circuit of an apparatus for identifying associated cell signaling proteins shown in FIG. 1.

Referring to FIG. 2, in this embodiment the apparatus 11 includes the memory 18, which includes a random access memory 20. The memory 18 further includes a permanent storage medium 22, which in this embodiment is a hard disk 23. Alternatively, other types of memory and/or storage media may be substituted.

The processor circuit 16 includes a microprocessor 24, in communication with the RAM 20, the hard disk 23 and the receiver 12 via a data bus 26.

Receiver

Referring to FIGS. 1 and 2, in this embodiment, the receiver 12 includes an input/output (I/O) unit 28 shown in FIG. 2. The I/O unit 28 is in communication one or more media drives, such as a floppy diskette drive 30 and a CD-RW drive 32, for example. The I/O unit is in further communication with a plurality of communication ports, including a serial port, a parallel port, an Ethernet interface and a modem, for example. Thus, receiving values representing physical properties of respective cell signaling proteins 14 may be achieved by receiving, at the I/O unit 28, data values read by a media drive from a computer-readable medium, such as a floppy diskette 34 for example. Alternatively, such data values may be received at the I/O unit 28 from a local device connected to one of the communications ports, or from a remote device such as an internet-based web server that stores such values, for example.

Production of Data Values

Data values representing the physical properties of cell signaling proteins may be obtained from commercial sources or may be obtained from preparing samples and employing equipment optionally included in the system shown in FIG. 1.

Referring back to FIG. 1, the system 10 may include a measuring device, such as the hardware 15, operable to produce the data values representing the physical properties of the respective cell signaling proteins. More particularly, in this embodiment the hardware 15 includes a chemiluminescence imager 300 operable to produce signals representative of proteins separated in a single dimension in an electrophoresis gel. In this embodiment the imager 300 includes a Fluor-S Max Multi-imager from Bio-Rad Laboratories Canada Ltd., of Mississauga, Ontario, Canada. The measuring device may further include an electrophoresis apparatus 302 operable to produce the electrophoresis gel. In this embodiment, the electrophoresis apparatus 302 includes a one-dimensional sodium dodecyl sulphate polyacrylamide gel electrophoresis (SDS-PAGE) measuring system.

Samples used to be tested for kinase or kinase substrate content may be any cell or tissue homogenate, extract or other such sample which has been processed to purify or partially purify kinases or kinase substrates in the sample. This technique is particularly suitable for testing patient biopsy samples. Such samples may be manipulated to increase prevalence of desired cell types or subcellular fractions in the sample. The sample will be typically prepared for electrophoresis using standard techniques, employing appropriate buffers which may contain various inhibitors or enzymes. For example, protease inhibitors may be present to reduce protein degradation on the sample. Where the sample is to be tested for kinase substrate content, it may be desirable to add one or more protein phosphatases to dephosphorylate substrates which may already exist in a phosphorylated state in the sample. The protein phosphatase will then be inactivated with an appropriate phosphatase inhibitor (e.g. β-glycerophosphate, sodium fluoride or sodium orthovanadate) and a selected protein kinase or mixture of protein kinases is then added to the sample to phosphorylate those substrates present which are specific to kinase added to the sample. Alternatively, endogenous kinases in the sample may be relied upon to phosphorylate dephosphorylated substrates in the sample.

SDS-PAGE employed in this technique is gel electrophoresis performed in a single dimension, typically using a slab shaped gel or a series of tube gels. The gel may be constructed and used employing standard methods, electrophoresis buffers and electrophoresis equipment. The gel may comprise a stacking gel and a separation gel. Commercial kits and equipment are available for performing SDS-PAGE. Preferable contents of the separation gel range from 10% to 15% (acrylamide) and 0.2 to 2% (bisacrylamide). For separation of kinases, an electric current will typically be applied to the gel until proteins with a molecular mass of less than about 25–27 kDa are eluted from the bottom of the gel as protein kinases do not have a molecular mass less than the latter amount.

Conventional wisdom calls for the use of two dimensional (2D) gel eletrophoresis to monitor changes in protein expression or post-translational modification of proteins. While it is possible to visualize some protein kinases on 2D gels by immunoblotting techniques, the inventor has discovered that in most cases, a maximum of only four or five protein kinases can be detected at a time by Western blotting of 2D gels with mixtures of protein kinase-specific antibodies. Furthermore, recovery of most protein kinases from a first dimension pH gradient gel, is less than 10%. That means that 90% of more of the protein kinases do not enter the second dimension gel and are therefore unresolved. The inventor's attempts to detect multiple kinases by immunoblotting 2D gels of rat brain lysates with multiple antibodies has demonstrated that 2D gel electrophoresis is insufficiently sensitive and inconsistently reproducible for the simultaneous detection of proteins as rare as cell signaling proteins.

Once electrophoresis is complete resulting in a pattern of separated protein moieties in the gel, the pattern is transferred to any membrane (e.g. nitrocellulose, PVDF, nylon, etc.) that is suitable for use in the Western Blotting technique. Transfer is typically done by standard electro-transfer techniques. Once the pattern is transferred to the membrane, the membrane may be cut into strips each of which will typically contain a pattern separated from a single sample (e.g. a test sample or a control sample). Alternatively, the membrane may be left intact for probing with a multiblotting apparatus such as MINIBLOTTER 20™, commercially available from Immunetics Inc. (Cambridge, Mass., USA).

Once the electrophoresis and Western blotting aspects of this method are complete, the resulting membrane or membrane strips are probed with a panel of different antibodies that react with distinct categories, subsets, isoforms, etc. of protein kinases or kinase substrates. The panel may be applied in one step as a mixture of antibodies or, the antibodies may be applied sequentially to the membrane. Binding of such antibodies to moieties present on the membrane is then detected using any suitable immunoassay procedure (e.g. see: Stites and Terr (eds) "Basic and Clinical Immunology", (7 ed) 1991). A particularly suitable procedure is to treat the antibodies in the panel as primary antibodies in a "sandwich" type assay. Unbound primary antibodies are washed away or otherwise removed. The membrane is then treated with secondary antibodies which are reactive with the primary antibodies. The secondary antibody may be bound to a detectable label or fused with an enzyme. Secondary antibody bound to primary antibody is detected by observing the label or the activity of the fused enzyme. Suitable labels and enzymes are known in the art and include magnetic or colored beads, fluorescent dyes, radiolabels, horseradish peroxidase, alkaline phosphatase, etc. The enzyme linked sandwich type assay (ELISA) is a particularly suitable methodology for use in this technique.

It is preferable that the panel of anti-kinase antibodies comprise polyclonal antibodies rather than MAB's. This departure from conventional wisdom increases the likelihood that new kinase proteins will be detected in the sample since polyclonal anti-kinase antibodies generally exhibit greater cross-reactivity to kinases as compared to anti-kinase MAB's. Despite the use of polyclonal antibodies, the panel may comprise from 2 to about 100 antibodies.

Antibodies for use in the method described herein may be obtained commercially or prepared using standard techniques. A variety of anti-kinase and anti-kinase substrate polyclonal antibodies are commercially available from various sources, including the following:

Biomol Research Laboratories, Inc. (Plymouth Meeting, Pa.)
Biosource International, Inc. (Camarillo, Calif.)
Promega Corporation (Madison, Wis.)
Santa Cruz Biotechnology (Santa Cruz, Calif.)
Sigma (Saint Louis, Mo.)
StressGen Biotechnologies Corp. (Victoria, British Columbia)
Transduction Laboratories (Lexington, Ky.)
Upstate Biotechnology Inc. (Lake Placid, N.Y.)
Zymed Laboratories Inc. (South San Francisco, Calif.)

Antibodies to new kinases may be prepared as described below. Typically, new kinases are partially purified by techniques such as column chromatography and SDS-PAGE. Microsequencing of partially purified kinases permits comparison to known kinases and possible development of immunological techniques for recovery of more of the new kinase by making use of cross reactivity with known antibodies. Antibodies can be raised against protein kinases or substrates in various host animals, including but not limited to cattle, horses, rabbits, goats, sheep and mice. Polyclonal antibodies can be obtained from immunized animals and tested for specificity using standard techniques. Alternatively, monoclonal antibodies may be prepared using any technique that provides for production of antibody molecules by continuous cell lines in culture, including the hybridoma technique of Kohler and Millstein, the human B-cell hybridoma technique, and the EBV-hybridomain technique. Alternatively, techniques for the production of single chain antibodies and antibody fragments that contain specific binding sites for a protein kinase or substrate may be generated by known techniques and employed in this technique. Such fragments include $F(ab')_2$ fragments that may be generated by digestion of an intact antibody molecule and Fab fragments that may be generated by severing disulfide bridges in $F(ab')_2$ fragments or through the use of Fab expression libraries.

Preferably, none of the antibodies in a given mixture to be used as a panel in this technique will cross-react with proteins that overlap in size. This may compromise interpretation of the experimental findings. Each antibody panel mixture should be blended to avoid such overlaps. Furthermore, every mixture should be adjusted for the concentration of each antibody so that there is optimal detection of the individual target kinases in diverse cell and tissue samples.

Following incubation of the strips with different mixtures of primary antibodies, the strips are incubated with a secondary antibody (e.g. a goat antibody that recognizes rabbit antibody) that reacts with the primary antibody. The secondary antibody is fused with an enzyme (e.g. alkaline phosphatase or horse radish peroxidase) to facilitate detection of the positions of the primary antibody, to which it binds by producing a light emission in an enzymatic reaction. The separate strips may be reassembled to appear in the order of the original membrane. The reassembled membrane may be subjected to enhanced chemiluminescence (ECL) and exposure to x-ray film or detected by a fluorescence imager (e.g. Fluor-S Max Multi-imager from Bio-Rad Laboratories Canada Ltd., of Mississauga, Ontario, Canada). In this indirect manner, the original positions of resolved protein kinases can be visualized as dark bands on a transparent background. The intensity of the bands can be quantized by densitometric analysis. In many cases, quantization of the amounts of a given protein kinases in the upper, phosphorylated form and the lower dephosphorylated form as resolved by SDS-PAGE can provide an accurate measurement of how much of the kinase is in the inactive and active states.

The method described herein offers advantages over standard 2D gel proteomic methods. This technique can be applied to any cell or issue sample. No prelabelling with radioisotopes is necessary, because kinase detection is based on immunoreactivity. The technology could be adapted for wide scale diagnostic applications because the patterns of protein kinase expression are stable for periods of up to six hours before an organ is subjected to fractionation and freezing, providing the organ is stored during this time over ice. This procedure can be carried out within two days from start to finish. By contrast, the 2D gel electrophoresis approach is extremely laborious, much more difficult to render and takes at least twice the time. This method provides the ability to compare multiple samples side by side. Whereas two or more samples can be analyzed on the same 1D gel, a 2D gel can only be used for a single sample. It is more difficult to compare two different samples by the 2D gel route, because of potential variations in the setting up, running and analysis of separate 2D gels.

One of the reasons why 2D gel electrophoresis has become the industry standard for proteomic analysis is the remarkable resolving power of the method and potentially thousands of spots can be distinguished on a 2D gel. Most of these spots, however, are "fuzzy" in appearance and may be overlapping. The method described herein provides much tighter protein bands with a 2- to 4-fold better resolution in the SDS-PAGE size-separation dimension. With detection based on immunoreactivity, the background of metabolic enzymes and structural proteins is essentially eliminated. This background is problematic even for 2D gel maps of phosphoproteins, since a third of all the proteins inside of cells appear to be phosphorylatable.

In one exemplary embodiment, about 50 µg of a control cell extract from untreated or healthy cells is loaded on to a SDS-PAGE gel in odd numbered lanes. In adjacent, even numbered lanes, equivalent amounts of experimental extracts are deposited. The latter samples are from cells that have been treated with a hormone or drug or that have been obtained from diseased tissue. The extracts may be prepared by homogenizing cells in buffer containing a detergent such as 0.5% Triton X-100™ and protein phosphatase inhibitors (to preserve the state of protein phosphorylation in the sample). The extracts are then subjected to ultracentrifugation to remove insoluble matter.

To optimize the detection of protein band shifts, the SDS-PAGE gel is precast with a higher than normal concentration of acrylamide and a lower than normal concentration of bisacrylamide. An electric current is applied to the slab gel until proteins with a molecular mass less than 27,000 Dalton are eluted from the bottom of the gel. The proteins remaining on the slab gel are then electro-transferred on to a nitrocellulose or PVDF membrane that traps the proteins. The membrane is cut into separate strips that each contain samples of the resolved proteins from both control and experimental cell extracts. Each strip is probed with a different mixture of primary antibodies (e.g. from rabbit) that react with a distinct subset peptide or protein substrate by the protein kinase of interest. Each reaction is conducted in a separate tube or well of a microtitre plate.

One application of this technique is for the discovery of novel protein kinases. The following strategy should permit the rapid acquisition of protein kinase drug targets. The objective of this approach is to identify those protein kinases that demonstrate increased expression or phosphorylation in association with a disease state or in response to an extracellular signal such as mitogen, drug or stress factor. The approach is based on the following:

1. Antibodies developed for one protein kinase can cross-react with structurally related protein kinases.
2. A band shift of a cross-reactive protein on an immunoblot is due to phosphorylation, and increased phosphorylation is probably associated with activation of the kinase. Greater than 90% of the known protein kinases are phosphorylated in their active states. One of the exceptions is glycogen synthase kinase-3, which is inhibited when it is phosphorylated on serine by protein kinase B. However, activation of glycogen synthase kinase-3 is still dependent on tyrosine phosphorylation of this kinase.
3. Proteins that cross-react with protein kinase antibodies and also bind to gamma-ATP-agarose beads have a very high probability of being protein kinases. This resin will capture many ATP binding proteins in addition to protein kinases but this procedure can purify kinases by up to 200-fold.
4. Proteins that autophosphorylate with [$\gamma$-$^{32}$P]ATP following immunoprecipitation with protein kinase antibody are likely to be protein kinases. Most antibodies are unsuitable for immunoprecipitation of proteins, and may require partial denaturation of the proteins. Denatured kinases would have little or no autophosphorylating activity.
5. A combination of gamma-ATP-agarose, immunosorbent and fast protein liquid chromatography column steps followed by SDS-PAGE permits rapid purification of an immunoreactive protein to allow for its identification by sequencing.
6. There is a likelihood that a protein kinase detected with antibodies is novel. Of the 2000 or so kinases expected to exist, only about a third have been fully sequenced. Nevertheless, partial cDNA sequences for most protein kinases are available in public and private EST cDNA sequence databases. Once a portion of the cDNA structure of the protein kinase gene is available, it is straightforward to obtain the complete nucleotide and amino acid structures of the gene and its protein with standard methodologies.

One of the beneficial outcomes of this technique is that unknown proteins which can cross-react with the kinase-specific antibodies are detected. Those unidentified proteins that change in their abundance or their phosphorylation state in response to a disease condition or treatment are worthy of closer inspection. If such proteins can be shown to bind to ATP-agarose or to be capable of autophosphorylation with radioactively labeled ATP, then there is a high probability that they are protein kinases. Moreover, it is possible to purify the protein so that it can be sequenced by the Edman degradation method or identified by mass spectroscopy of trypsin digested fragments of the protein. Purification is best done using the antibody that was originally used to detect the putative kinase. If any part of the protein has been previously sequenced, it would be available in public or private protein sequence databases. A partial sequence in the human EST sequence database may be available. From this information, a full length cDNA sequence for the protein could be rapidly obtained using PCR-based techniques. This would be worthwhile if the cDNA sequence contained conserved kinase catalytic subdomain sequences. In this manner, novel protein kinases that display desirable characteristics (e.g. increased expression in solid tumor relative to adjacent, normal tissue) can be detected and identified. If the inappropriate activity of such protein kinase is shown to contribute to the development of the disease, then they would be most valuable drug targets.

Initial detection of measurement of the activation of a protein kinase in the methods described herein is dependent on the detection of its band shift on SDS-PAGE gels. Phosphorylated forms often appear to be 0.5 to 2 kDa larger than their dephosphorylated counterparts. In a small number of cases, phosphorylation is indicative of inactivation of a kinase. A limited number of protein kinases do not exhibit a band shift change when they are activated. However, their in vivo substrates can display band shifts upon their phosphorylation. This can be exploited for the development of in vitro and in vivo substrate assays. Current approaches for high throughput screening of protein kinase inhibitors in vitro involve the use of radioactive [$\gamma$-$^{32}$]ATP and measurement of the incorporation of the radioactive phosphate into a peptide or protein substrate by protein kinase of interest. Each reaction is conducted in a separate tube or well of a microtitre plate generating high volumes of radioactive garbage.

There are many examples of proteins that are highly specific substrates of particular protein kinases; examples include glycogen phosphorylase for phosphorylase kinase, myosin light chain for myosin light chain kinase, eIF2α for PKR, MARCKS for protein kinase C, Erk1 and Erk2 for Mek1 and Mek2. Antibodies are commercially available for many of these substrates or may be produced as described above. Such antibodies may be used to probe for the phospho-states of the substrates, as revealed by their mobility on immunoblots of SDS-PAGE gels. These substrates would not have to be purified from crude cellular extracts for use in the protein kinase assays. However, since many of the substrates may already exist in phosphorylated forms in cell extracts, it may be necessary to incubate the extracts with active preparations of protein phosphatases, which can be subsequently inactivated with phosphatase inhibitors prior to the kinase assays. With this method, a crude mixture of active protein kinases may be added to the phosphatase-treated cellular extract in a single tube, and the phosphorylation reaction can commence with the inclusion of non-radioactive ATP. Only catalytic amounts of protein kinases will be necessary, so any phosphorylated substrates that contaminate the preparation of protein kinases will be relatively minor compared to the amounts of the substrates in the phosphatase-treated cell extracts. Any kinases that contaminate the phosphatase-treated cell extracts would not be a concern, since they are actually desirable. It may be necessary to add a kinase preparation after phosphatase treatment of the substrate extracts, because many protein kinases are inhibited when they are dephosphorylated. After a short suitable incubation time, the reactions can be terminated by addition of SDS-PAGE sample buffer. Such substrate analysis can be performed as described above for protein kinases, except that panels of antibodies for the kinase substrates will be used in place of the kinase antibody panels. By this approach, the decreased mobility of the kinase substrates will be evident as band shift on the immunoblots in the absence of kinase inhibitors. The presence of specific protein kinase inhibitors would be revealed by the inhibition of the appearance of the upper bands.

In vitro substrate analysis according to the methods described herein would be ideal for the further characterization of compounds that have already been shown to display inhibitor activity toward a kinase and the selectivity of these compounds is in question. A distinct advantage of this method is that it would be easy to compare the findings with a substrate analysis in vivo assay performed using the same blends and concentrations of kinase substrate antibodies that work in the in vitro kinase assay. However, the analysis would be performed on extracts from cells that have been incubated with agonists that stimulate the kinases of interest. These cells would also be exposed to the compounds that exhibit inhibitory activity towards kinase in vitro. In this manner, the efficacy of these inhibitors could be evaluated in living cells.

The intensity of the signal that is generated for a protein kinase band may be readily quantified using known technologies. For example, quantification may be done by using a Fluor-S Max Multi-imager from Bio-Rad Laboratories Canada Ltd., of Mississauga, Ontario, Canada. This equipment can quantize changes in band intensity in range of 1:100,000 but 1:1,000 is more typical. Multiple exposures of X-ray films to ECL for detection of immunoreactive bands to compensate for any non-linearity of response of the film prior to quantization by densitometric analysis could be performed as an alternative method.

Each immunoreactive band is assigned a set of parameters that includes its relative optical density, molecular weight and immunoreactivity. The relative optical density (R.O.D.) value of an immunoreactve protein band is based on the ratio of the intensity of that protein relative to the intensity of a protein kinase band that serves as an internal control. For example, the mitogen-activated protein (MAP) kinase Erk1 in 50 µg of rat brain cytosolic protein detected with Erk1-CT antibody could serve as such an internal control. Erk1 has been found to be one of the most uniformly expressed protein kinases in different rat tissues and diverse organisms. Alternative standards could be the zeta isoform of protein kinase C or the alpha isoform of p38 Hog MAP kinase. If a protein has the same intensity on a Western blot as Erk1 in rat brain, then it has an R.O.D. value of 100.

Another parameter is the molecular mass of an immunoreactive protein band, which is based on its migration on the SDS-PAGE gel relative to known molecular mass marker proteins such as phosphorylase, bovine serum albumin, ovalbumin, glyceraldehyde 3-phosphate dehydrogenase and lysozyme.

A further parameter is the immunoreactivity of a protein band, which is somewhat selective, and particularly appropriate when the immunogen to which the antibody was originally developed is considered. For example, an antibody developed against the C-terminal 40 amino acids of the rat brain Erk1 isoform would be expected to immunoreact with the full-length 44 kDa form of Erk1 on Western blots of rat brain cytosol.

Determination of the structure of a protein kinase network is based on the following principles.

i. Modules of protein kinases have been highly conserved in the evolution of diverse eukaryotes. These modules mediate the transmission of information in signaling pathways.

ii. Protein kinases that operate within a common module would be typically coexpressed in cells found in different tissues and species.

iii. Protein kinase networks are formed from the interconnection of diverse protein kinase modules. This implies extensive crosstalk between signaling modules.

iv. An upward shift in a protein kinase band due to reduced mobility reflects its regulation, most likely marking its activation. If other protein kinase bands are similarly affected by the same set of cell stimuli, then they may operate within the same module.

v. The higher the correlation between two protein bands with respect to their coexpression and their band shifting in response to a wide diversity of stimuli, the closer that they operate within a common signaling module. Protein kinases that are not coexpressed and do not undergo coregulation, are not connected in the same pathway.

Determination of the architecture of a protein kinase network requires the examination of a wide range of different cell types and perturbations. Ideally, at least one hundred different experimental model systems should be analyzed. It is important that while extremely diverse model systems are explored, the methods and probes for the Western blotting analysis are uniformly consistent. By testing the regulation of the same group (e.g. 100) of different protein kinases in a several diverse model systems with a wide range of different perturbations, each immunoreactive band can be separately compared with each of the other hundred or more immunoreactive bands for (1) the intensity of the signals and (2) whether the protein kinases are similarly altered in their phosphorylated states.

It is noteworthy that values representing physical properties of kinases have not been readily available in the past. Accordingly, the above description illustrates a method of detecting multiple kinases or multiple kinase substrates, to obtain data values representing physical properties of kinases, in the event that such data cannot be conveniently received from commercial sources such as internet-based web servers, compact discs or other media, for example. Once the procedures described above have been performed, to produce a one-dimensional electrophoresis gel such as that shown at 13 in FIG. 1, existing hardware 15 and software (not shown) may be used to measure the gel to produce digital data values representing the physical properties of the kinases, such as their amounts in phosphorylated and dephosphorylated states respectively, for example. Such software preferably produces such digital data and stores it on the floppy diskette 34 or other medium, in a MICROSOFT EXCEL™ spreadsheet table format readable by EXCEL 98™ software from Microsoft Corporation, Redmond, Wash., USA, however, other formats may be substituted. An example of suitable software for densitometric quantization of chemiluminescence generated by ECL from a Western blot of target proteins is the QUANTITY ONE™ software from Bio-Rad Laboratories Canada Ltd., of Mississauga, Ontario, Canada.

Configuration of Data Processing System

Referring to FIG. 2, in this embodiment the storage medium 22 acts as a computer readable medium for providing instructions for directing a programmable device to perform various functions described herein. In this regard, the storage medium 22 stores a plurality of routines, each routine including blocks of instruction codes which configure or program the processor circuit 16 to perform such functions. Alternatively, such blocks of instruction codes may be obtained as segments of a signal embodied in a carrier wave received at the processor circuit. One group of the blocks of instruction codes, for example, provides a receive data routine 36 which configures the processor circuit 16 to cooperate with the receiver 12 to receive data values representing physical properties of respective cell signaling proteins 14.

A coexpression routine 40 configures the processor circuit to produce, as the comparison values, a coexpression coefficient for each pair of the cell signaling proteins, each coexpression coefficient representing a degree of coexpression of one cell signaling protein of the pair and the other cell signaling protein of the pair. The coexpression routine also configures the processor circuit to normalize the data values relative to at least one reference value, prior to producing the comparison values.

A coregulation routine 42 configures the processor circuit to produce, as the comparison values, a coregulation coefficient for each pair of the cell signaling proteins, each coregulation coefficient representing a degree of coregulation of one cell signaling protein of the pair and the other cell signaling protein of the pair.

A linkage routine 44 configures the processor circuit to produce, as the comparison values, a linkage coefficient for each pair of the cell signaling proteins, as a function of a coexpression coefficient representing a degree of coexpression of one cell signaling protein of the pair and the other cell signaling protein of the pair, and of a coregulation coefficient representing a degree of coregulation of the one cell signaling protein of the pair and the other cell signaling protein of the pair, each linkage coefficient representing a degree of association between the one cell signaling protein and the other cell signaling protein.

A clustering subroutine 46 configures the processor circuit to identify a cluster of associated cell signaling proteins, by identifying a group of pairs of associated cell signaling proteins for which each member of each pair is present in at least one other pair of the group.

The various instruction codes stored in the storage medium 22 further configure the processor circuit 16 to define, in the RAM 20, a plurality of buffers, registers and stores. For example, referring to FIGS. 1 and 2, the processor circuit 16 is directed to define in the RAM 20, a program store 50 for temporarily storing the various routines or portions thereof for execution by the processor circuit and for providing a temporary calculation area, a clustering pointers register 51 for storing pointers for use by the clustering subroutine 46, and a display buffer 52 for storing data representing an image to be displayed on a display such as that shown at 53 in FIG. 1.

Referring again to FIG. 2, the processor circuit 16 is further directed to define the following additional stores in the RAM 20. An input data values store 54 is used to store received data values representing physical properties of respective cell signaling proteins, which in this embodiment are kinases. A total per protein (TPP) data store 56 is used to store data representing total amounts of respective cell signaling proteins (in this embodiment, kinases), irrespective of the phosphorylation states of such signaling proteins. First and second normalized data stores 58 and 60 are used to store data representing normalized cell signaling protein data values. A state data store 61 stores data representing phosphorylation states of the cell signaling proteins. A coexpression coefficients store 62 is used to store a coexpression coefficient for each pair of the cell signaling proteins. A coexpressed pairs store 64 stores a list of coexpressed cell signaling protein pairs, and a coexpressed clusters store 66 stores a list of clusters of the coexpressed cell signaling protein pairs. Similarly, a coregulation coefficients store 68 is used to store a coregulation coefficient for each pair of the cell signaling proteins, a coregulated pairs store 70 stores a list of coregulated cell signaling protein pairs, and a coregulated clusters store 72 stores a list of clusters of the coregulated cell signaling protein pairs. A linkage coefficients store 74 stores a linkage coefficient for each pair of the cell signaling proteins. A linkagesorted pairs store 76 stores a list of cell signaling protein pairs sorted by their linkage coefficients, and a linked pathway groups store 78 stores a plurality of groups of cell signaling proteins associated with common signaling pathways.

Operation

Generally, the present embodiment of the invention involves producing and storing a comparison value for each pair of cell signaling proteins in response to data values representing physical properties of respective cell signaling proteins, such as the amounts or quantities of the cell signaling proteins detected in respective biological samples, and/or phosphorylation states of the cell signaling proteins, for example. Cell signaling protein pairs having comparison values satisfying a condition indicative of an association between the cell signaling proteins are then identified.

A number of different techniques may be used to produce the comparison values, with the result that a number of corresponding conditions indicative of associations between the cell signaling proteins may be applied.

For example, if a first kinase tends to be present whenever a second kinase is present, such kinases are likely to be associated. Thus, one way of producing comparison values includes producing a coexpression coefficient for each pair of the cell signaling proteins, representing a degree of coexpression of one cell signaling protein of the pair and the other cell signaling protein of the pair.

Similarly, if two kinases tend to be found in the same phosphorylation state, such kinases are likely to be commonly regulated and are therefore also likely to be associated with each other. Thus, a second way of producing comparison values includes producing a coregulation coefficient for each pair of the cell signaling proteins, representing a degree of coregulation of one cell signaling protein of the pair and the other cell signaling protein of the pair.

Either of the above methods of producing comparison values may be used by itself, independently of the other. However, the present embodiment of the invention further provides a third method of producing comparison values, by combining the results of the coexpression and coregulation analyses, to produce a linkage coefficient for each cell signaling protein pair as a function of the coexpression and coregulation coefficients for the pair. Using the linkage coefficients, cell signaling proteins may then be associated with respective common signaling pathways.

Alternatively, other methods of producing comparison values may be apparent to one of ordinary skill in the art upon reading this specification and are not considered to depart from the scope of the present invention.

Receive Data Routine

Figure 3:
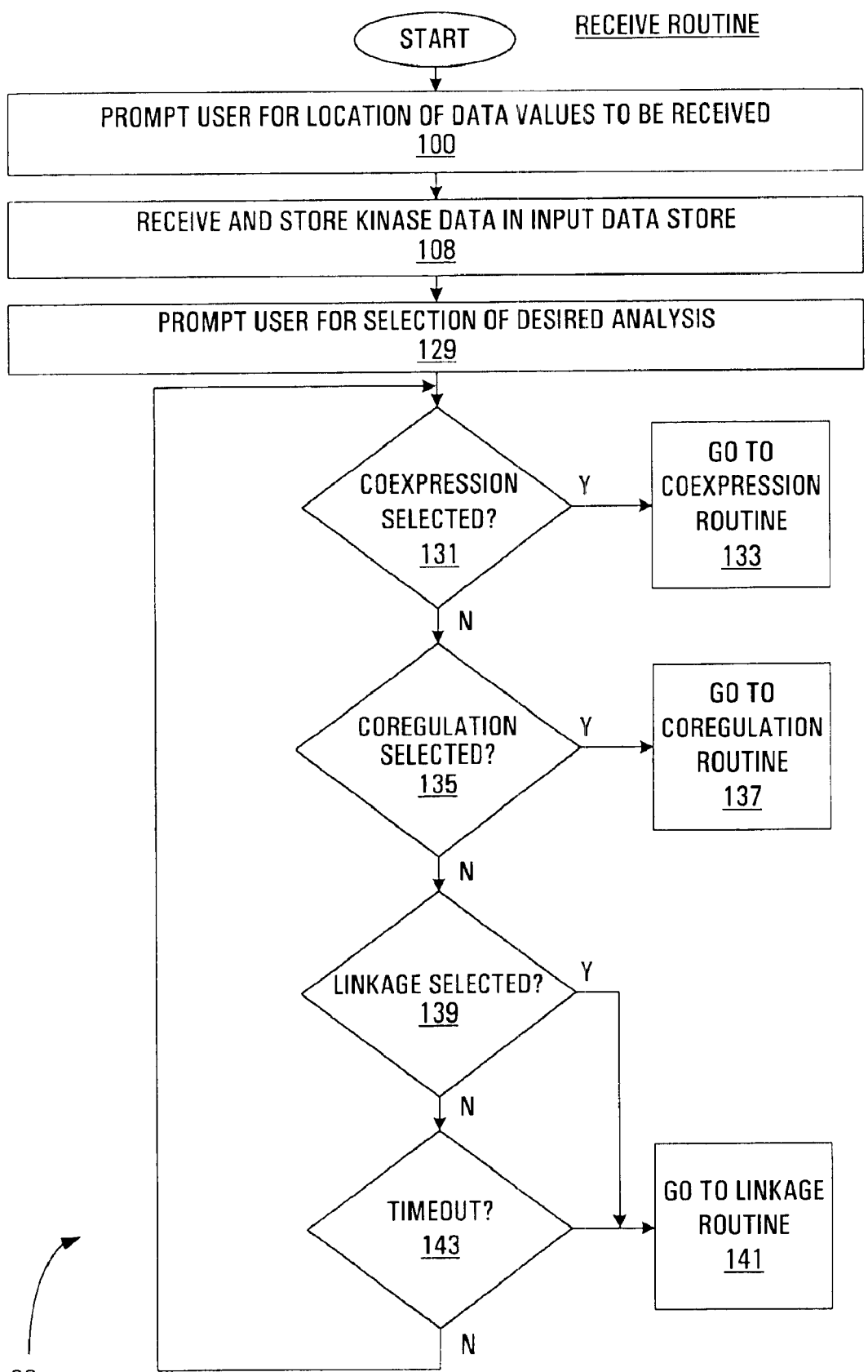
FIG. 3 is a flowchart of a receive data routine executed by the processor circuit shown in FIG. 2.

Referring to FIGS. 2, 3 and 4, the operation of the present embodiment of the invention begins with execution of the receive data routine 36 by the processor circuit 16. The receive data routine 36 includes a plurality of blocks of instruction codes that configure or program the microprocessor 24 to cooperate with the I/O unit 28 to act as a receiver operable to receive data values representing physical properties of respective cell signaling proteins. More particularly, in this embodiment the microprocessor and I/O unit cooperate to receive sets of cell signaling protein data, each set including data values representing amounts of respective corresponding cell signaling proteins in biological material corresponding to the set, and further including data values indicative of phosphorylation states of respective cell signaling proteins in biological material corresponding to the set. Although it is preferable to receive such data, indicative of both the amounts and the phosphorylation states of the cell signaling proteins, alternatively, significant benefits may be achieved even if the data is indicative of only one of these two exemplary physical properties.

Referring to FIGS. 1, 2 and 3, the receive data routine 36 begins with a first block of codes 100 shown in FIG. 3, which directs the processor circuit 16 to control the display 53 to prompt a user of the apparatus 11 to enter information representing a location from which the desired kinase data values or other cell signaling protein data values may be received. Such information may be entered by the user via a user interface device such as a keyboard 102 or a mouse 104 shown in FIG. 1, for example. The information may include a file path, such as a:/kinasedata.xls or d:/kinasedata.xls for example, indicating that the data values are to be received from an EXCEL (™) spreadsheet file stored on either the floppy diskette 34 or a compact disc 35, via the floppy diskette drive 30 or the CD-RW drive 32 respectively. Or, if the user has chosen to actually produce the desired data values, the information may include an identification of the hardware 15 to direct the processor circuit to receive the data values directly from the hardware 15, via a cable 106 such as a parallel port cable for example, connecting the hardware to the I/O unit 28. Alternatively, the information may include any other location information, such as a Universal Resource Locator (URL) or an Internet Protocol (I.P.) address for example, indicating a location on a network such as the Internet from which the data values may be downloaded via the I/O unit 28.

After receiving user input providing such location information, block 108 directs the microprocessor 24 to cooperate with the I/O unit 28 to receive the data values from the specified location, such as an EXCEL (™) spreadsheet file stored on the floppy diskette 34 for example, and to store the data values in the input data values store 54 in the RAM 20. In this embodiment, block 108 further directs the processor circuit 16 to copy the newly-stored contents of the input data values store 54 to a data storage area 110 in the storage medium 22 for permanent storage therein, in the event that subsequent re-analysis of the data values may be desired at a later date.

Referring to FIG. 4, the structure and contents of the input data values store immediately following execution of block 108 are illustrated generally at 54. For each cell signaling protein, a cell signaling protein data record 112 is defined, having an identification field 114 containing an identification of the particular cell signaling protein, such as "A", "B" or "Erk1", for example. The remainder of the cell signaling protein data record 112 is divided into a phosphorylated sub-record 116 and a dephosphorylated sub-record 116. Each of the sub-records 116 and 118 includes a plurality of information fields. A phosphorylation state field 120 contains an identification of a phosphorylation state of the cell signaling protein, such as "P" or an active bit to indicate a phosphorylated state, or a "D" or an inactive bit to indicate a dephosphorylated state, for example. Each sub-record then contains a plurality of measurement fields 122, each measurement field corresponding to a particular set of data values or measurements of all cell signaling proteins identified in the input data values store 54.

For illustrative purposes, in this embodiment only ten sets of data values corresponding to ten respective measurements of the cell signaling proteins in ten respective biological samples are received and analyzed, however, it will be appreciated that a much larger number of measurements, such as 100 separately measured model systems for example, is desirable in order to improve the statistical reliability of the results. Therefore, in this embodiment each phosphorylated sub-record 116 includes ten phosphorylated measurement fields 124, each containing a measurement of an amount of the cell signaling protein detected in a phosphorylated state, and similarly, each dephosphorylated sub-record 118 includes ten dephosphorylated measurement fields 126, each containing a measurement of an amount of the cell signaling protein detected in a dephosphorylated state.

Alternatively, if a user desires to obtain only coexpression information, without coregulation or linkage information, each cell signaling protein data record 112 may contain only a single measurement field 122 for each measurement set or model system, the measurement field 122 containing a measurement of a total detected amount of the corresponding cell signaling protein, irrespective of its phosphorylation state. Conversely, if a user desires to obtain only coregulation information, without coexpression or linkage information, each cell signaling protein data record 112 may contain only a single measurement field 122 for each measurement set or model system, the measurement field 122 containing an indication of the phosphorylation state in which the corresponding cell signaling protein was detected, irrespective of the amount that was detected.

Referring back to FIG. 3, following such receipt and storage of data values at block 108, block 129 directs the processor circuit 16 to control the display 53 to prompt the user of the apparatus 11 to select a desired analysis, such as coexpression, coregulation or linkage analysis, for example. Block 131 then directs the processor circuit 16 to determine whether user input selecting coexpression has been entered, in which case block 133 directs the processor circuit to execute the coexpression routine 40 shown in FIG. 5.

Figure 13:
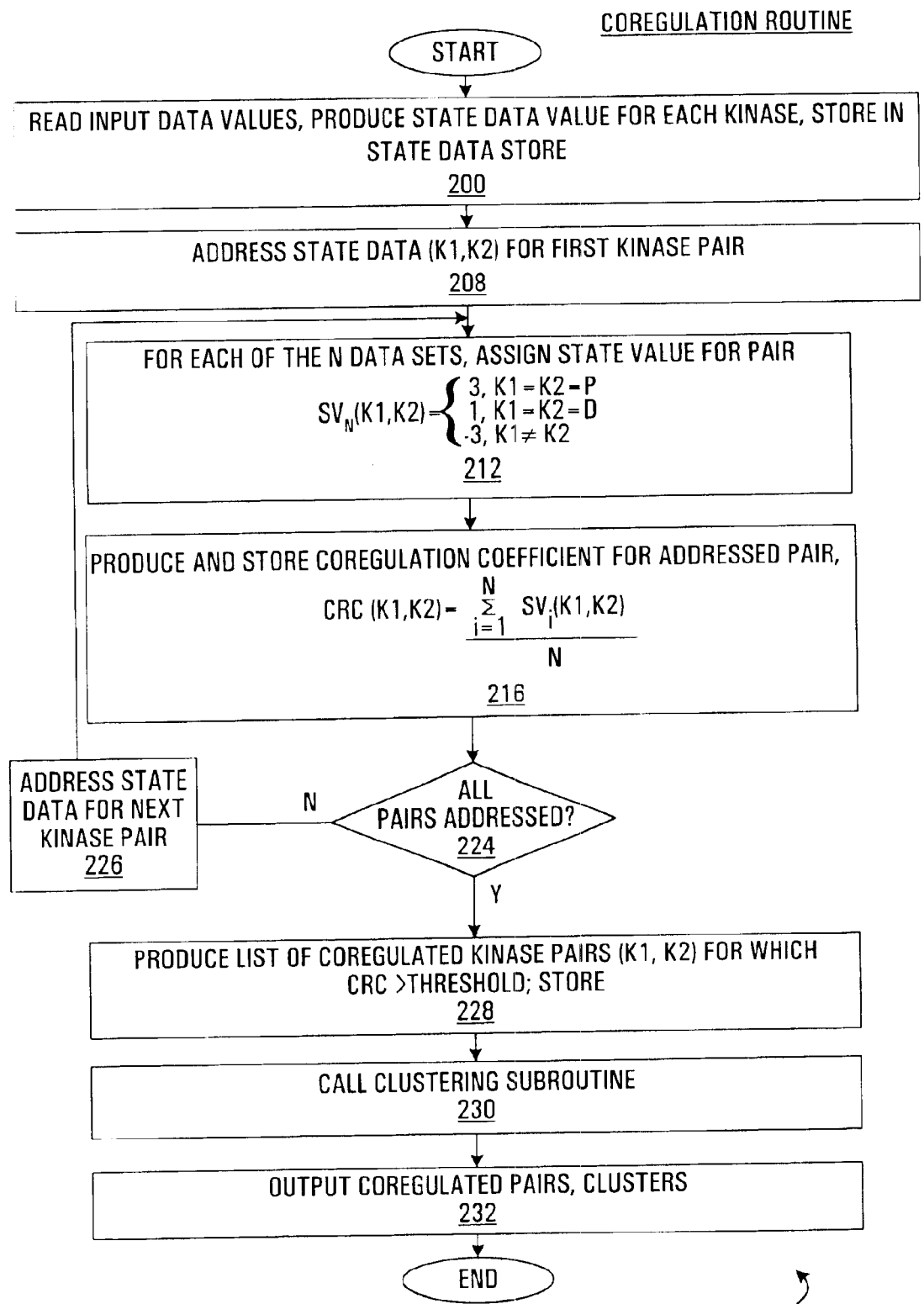
FIG. 13 is a flowchart of a coregulation routine executed by the processor circuit shown in FIG. 2.

Referring back to FIG. 3, similarly, block 135 directs the processor circuit to determine whether user input selecting coregulation has been entered, in which case block 137 directs the processor circuit to execute the coregulation routine 42 shown in FIG. 13. Referring back to FIG. 3, if at block 139 the processor circuit determines that user input selecting linkage has been entered, block 141 directs the processor circuit to execute the linkage routine 44 shown in FIG. 18. Referring back to FIG. 3, similarly, if at block 143 the processor circuit has failed to receive any user input within a pre-defined timeout period, the processor circuit is directed to execute the linkage routine 44 by default. If the timeout period has not elapsed, processing continues through blocks 129 to 143. Following such direction at either block 133, 137 or 141, the receive data routine 36 is ended.

Coexpression Routine

Figure 5:
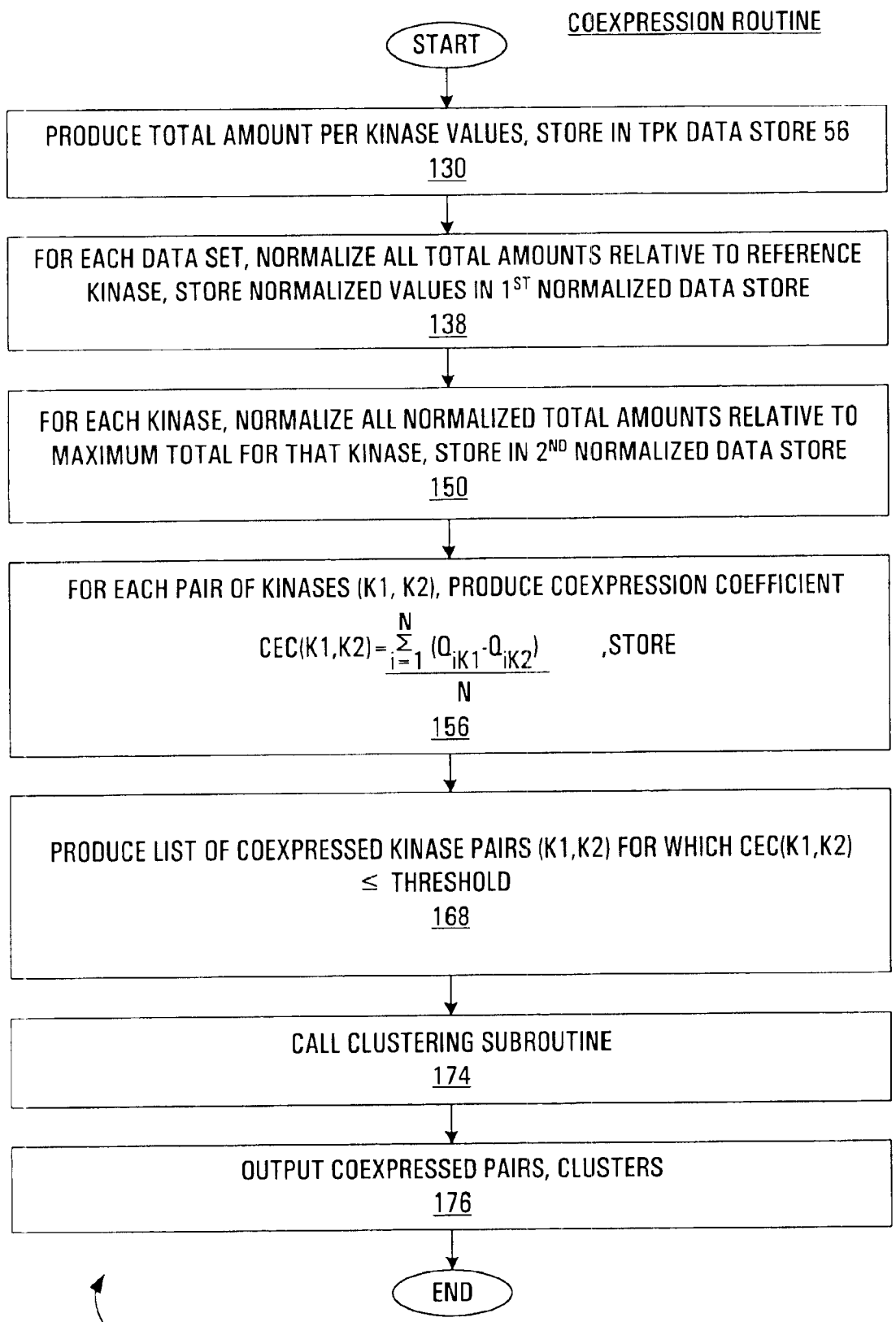
FIG. 5 is a flowchart of a coexpression routine executed by the processor circuit shown in FIG. 2.

Referring to FIGS. 5 to 11, the coexpression routine is shown generally at 40 in FIG. 5. Generally, the coexpression routine 40 configures the processor circuit 16 to produce and store, in the memory 18, a comparison value for each pair of the cell signaling proteins in response to the received cell signaling protein data values, and to identify cell signaling protein pairs having comparison values satisfying a condition indicative of an association between the cell signaling proteins. More particularly, the coexpression routine configures the processor circuit to produce, as the comparison values, a coexpression coefficient for each pair of the cell signaling proteins, each coexpression coefficient representing a degree of coexpression of one cell signaling protein of the pair and the other cell signaling protein of the pair.

Referring to FIGS. 2, 4, 5 and 6, the coexpression routine 40 begins with a first block of codes shown at 130 in FIG. 5, which directs the processor circuit 16 to read the contents of the input data values store 54 shown in FIG. 4, and to use such contents to produce total amount per protein values and store such values in the total per protein (TPP) data store 56 shown in FIG. 6.

Referring to FIG. 6, in this embodiment the TPP data store 56 contains a plurality of protein total amount records 132. Each protein total amount record 132 includes an identification field 134 for storing an identification of the cell signaling protein, and a plurality of total amount fields 136, each total amount field 136 containing a number representing a total detected amount of the cell signaling protein in a particular corresponding measurement set or model system.

Referring to FIGS. 4, 5 and 6, block 130 directs the processor circuit 16 to sequentially address each cell signaling protein data record 112 stored in the input data values store 54. For each such addressed cell signaling protein data record 112, block 130 directs the processor circuit to sequentially address each set of data measurements. For each such addressed set, block 130 directs the processor circuit to add the contents of the phosphorylated measurement field 124 and the dephosphorylated measurement field 126 of the currently addressed cell signaling protein data record 112, and to store this sum in a total amount field 136 shown in FIG. 6, corresponding to the currently addressed set of data measurements, of a protein total amount record 132 corresponding to the currently addressed cell signaling protein data record 112.

Referring to FIGS. 5, 6 and 7, block 138 then configures the processor circuit to normalize the values stored in the TPP data store 56, relative to at least one reference value, prior to producing the comparison values. It will be appreciated that the experimental sensitivity of each measurement set or model system may vary from set to set. Accordingly, it is desirable to normalize each set of cell signaling protein data by expressing each data value in the set relative to a particular reference value in the set that corresponds to a cell signaling protein or other detected protein that is expected to be present in a roughly identical amount in all measurement sets or model systems.

Thus, referring to FIG. 6, for each data set 140 in the TPP data store 56, the contents of each total amount field 136 of the data set 140 are expressed relative to the contents of a reference measurement field 142 of a reference total amount record 144. More particularly, in this embodiment, the reference total amount record 144 includes ten reference measurement fields 142, one for each data set 140, the contents of each reference measurement field 142 representing a total amount of Erk1, detected with an Erk1-CT antibody. To achieve this relative expression, block 138 directs the processor circuit 16 to divide each amount stored in each total amount field 136 of a particular data set 140, by one percent of the contents of the reference measurement field 142 of that data set 140. For example, if the contents of the reference measurement field 142 for the data set are equal to 200, the contents of each total amount field 136 of that data set are divided by two.

Referring to FIGS. 2, 5 and 7, block 138 further directs the processor circuit 16 to store such normalized values in corresponding once-normalized measurement fields 146 of corresponding once-normalized cell signaling protein data records 148 in the first normalized data store 58.

Referring to FIGS. 2, 5, and 7 and 8, block 150 then directs the processor circuit 16 to further normalize the total amount values by expressing each total amount for a given cell signaling protein as a percentage of the maximum amount of that particular cell signaling protein detected in any of the ten measurement sets. To achieve this, block 150 first directs the processor circuit to successively address each once-normalized cell signaling protein data record 148 in the first normalized data store 58. For each such addressed record 148, block 150 directs the processor circuit to produce a maximum normalized amount value equal to the maximum quantity stored in any of the ten once-normalized measurement fields 146 of the particular once-normalized cell signaling protein data record 148.

Block 150 further directs the processor circuit to store this maximum value in a maximum normalized amount field 151 of the once-normalized cell signaling protein data record 148. Block 150 then directs the processor circuit to divide the contents of each once-normalized measurement field 146 of the currently addressed record 148 by one percent of the contents of the maximum normalized amount field 151 of the addressed record 148. Block 150 further directs the processor circuit to store the resulting quantity in a twice-normalized measurement field 152 of a twice-normalized cell signaling protein data record 154 in the second normalized data store 60, the record 154 corresponding to the currently addressed once-normalized cell signaling protein data record 148. Block 150 continues to successively address once-normalized cell signaling protein data records 148 in this manner until such twice-normalized values have been produced and stored in each twice-normalized measurement field 152 of each twice-normalized cell signaling protein data record 154.

Referring to FIGS. 2, 5, 8 and 9, block 156 then directs the processor circuit 16 to produce, as the comparison values, a coexpression coefficient for each pair of the cell signaling proteins, each coexpression coefficient representing a degree of coexpression of one cell signaling protein of the pair and the other cell signaling protein of the pair. To achieve this, block 156 configures the processor circuit to successively address each possible pair of cell signaling proteins identified in respective twice-normalized cell signaling protein data records 154 stored in the second normalized data store 60, such as an exemplary cell signaling protein pair 158 shown in FIG. 8 consisting of the kinases identified as "M" and "O", for example. For each such addressed cell signaling protein pair 158, block 156 configures the processor circuit to calculate, for each of the ten data sets 160 in the second normalized data store 60, a difference value equal to an absolute value of a difference between a data value stored in the twice-normalized measurement field 152 corresponding to one cell signaling protein of the addressed pair 158, and a data value stored in the twice-normalized measurement field 152 corresponding to the other cell signaling protein of the addressed pair 158.

Once all ten such difference values for the ten respective data sets 160 have been calculated for the currently addressed pair 158, block 156 further configures the processor circuit to add the ten difference values for each of the sets to produce a sum of difference values. Block 156 then configures the processor circuit to divide this sum by the number of the sets (in this embodiment, ten) to produce the coexpression coefficient corresponding to the one cell signaling protein and the other cell signaling protein of the currently addressed cell signaling protein pair 158.

Referring to FIGS. 5 and 9, block 156 further directs the processor circuit 16 to store this coexpression coefficient in the coexpression coefficients store 62, or more particularly, in a coexpression coefficient field 162 of a cell signaling protein coexpression record 164 corresponding to the first cell signaling protein of the currently addressed pair 158. As shown in FIG. 9, each cell signaling protein coexpression record 164 includes a cell signaling protein identification field 166, and further includes a plurality of coexpression coefficient fields 162, containing a plurality of respective coexpression coefficients corresponding to the coexpression of the cell signaling protein identified in the identification field 166 and every other successive cell signaling protein (e.g. every kinase whose corresponding coexpression record 164 appears beneath the current coexpression record 164 in the coexpression coefficients store 62 shown in FIG. 9). It will be appreciated that for the purpose of analyzing coexpression, it is unnecessary to treat the cell signaling protein pairs as permutations rather than combinations, as the coexpression of kinase M with O for example is necessarily identical to the coexpression of O with M. However, if desired, each coexpression record 164 may redundantly contain coexpression coefficients for the identified cell signaling protein and all other cell signaling proteins, rather than merely successive proteins. Block 156 continues to direct the processor circuit to produce and store coexpression coefficients in this manner, until a coexpression coefficient has been produced and stored for every possible pair of cell signaling proteins. Finally, block 156 directs the processor circuit to produce and store, in the data storage area 110 of the storage medium 22, a copy of the coexpression coefficients store 62, in the event that it is desired to subsequently retrieve such information.

Referring to FIGS. 2, 5, 9 and 10, block 168 configures the processor circuit 16 to identify cell signaling protein pairs having comparison values satisfying a condition indicative of an association between the cell signaling proteins, and to produce a list of pairs of associated cell signaling proteins. More particularly, block 168 configures the processor circuit to identify the cell signaling protein pairs by identifying each cell signaling protein pair having a coexpression coefficient less than or equal to a threshold coexpression value. In this embodiment, where the cell signaling proteins are kinases, for the purpose of coexpression, the condition indicative of an association between two kinases is satisfied if the coexpression coefficient for those two kinases is less than or equal to 15.

Thus, block 168 configures the processor circuit 16 to read the contents of each of the coexpression coefficient fields 162 in the coexpression coefficients store 62, and to produce a list of coexpressed cell signaling protein pairs such as that shown in FIG. 10, the list including an identification of each cell signaling protein pair having a coexpression coefficient less than or equal to the threshold coexpression value, which in this embodiment is 15. Alternatively, other threshold values may be substituted. As an illustrative example, as shown in FIG. 10, block 168 directs the processor circuit to include in the list of coexpressed pairs, an identification 172 of an exemplary cell signaling protein pair 170 shown in FIG. 9 consisting of the kinases B and C, for which the coexpression coefficient is 9. Block 168 further directs the processor circuit to store the list of identifications of coexpressed pairs in the coexpressed pairs store 64 shown in FIG. 2, and to store a copy of the coexpressed pairs store 64 in the data storage area 110 of the storage medium 22 for subsequent retrieval, if desired.

Block 174 then directs the processor circuit 16 to call the clustering subroutine 46, and to store, in the clustering pointers register 51, respective pointers to the coexpressed pairs store 64 and the coexpressed clusters store 66, to indicate that the input data to the clustering subroutine is stored in the coexpressed pairs store, and that the output of the clustering subroutine is to be written to the coexpressed clusters store.

Finally, block 176 directs the processor circuit 16 to output the list of coexpressed cell signaling protein pairs stored in the coexpressed pairs store 64, as shown in FIG. 10, and the list of coexpressed cell signaling protein clusters stored in the coexpressed clusters store 66, a shown in FIG. 11. Such output may include generating a printout of these lists on a printer (not shown) in communication with the processor circuit via the I/O unit 28 for example, and/or displaying such lists on the display 53 shown in FIG. 1. Alternatively, such output may include writing the contents of the coexpressed pairs store and the coexpressed clusters store to a medium such as the floppy diskette 34 shown in FIG. 1, via the I/O unit 28 and the floppy diskette drive 30, or to other media, or may include communicating such contents to a remote device via a network such as an intranet or the Internet. Alternatively, other types of outputs may be substituted.

It will be appreciated that the output contents of the coexpressed pairs store 64 and the coexpressed clusters store 66, as shown in FIGS. 10 and 11, suggest the following conclusions. Kinases A, B, C and D, which form a common cluster, are commonly coexpressed and may operate together in a signaling pathway. Kinases I, J, K and L, which also form a common cluster, are commonly coexpressed and may operate together in a signaling pathway. Kinases M, N, O and P, which also form a common cluster, are commonly coexpressed and may operate together in a signaling pathway. Similarly, Kinases Q, R, S and T, which also form a common cluster, are commonly coexpressed and may operate together in a signaling pathway. Kinases E and F are commonly coexpressed and may operate together in a signaling pathway. Kinases G and H are commonly coexpressed and may operate together in a signaling pathway.

The coexpression routine 40 is then ended.

Clustering Subroutine

Figure 12:
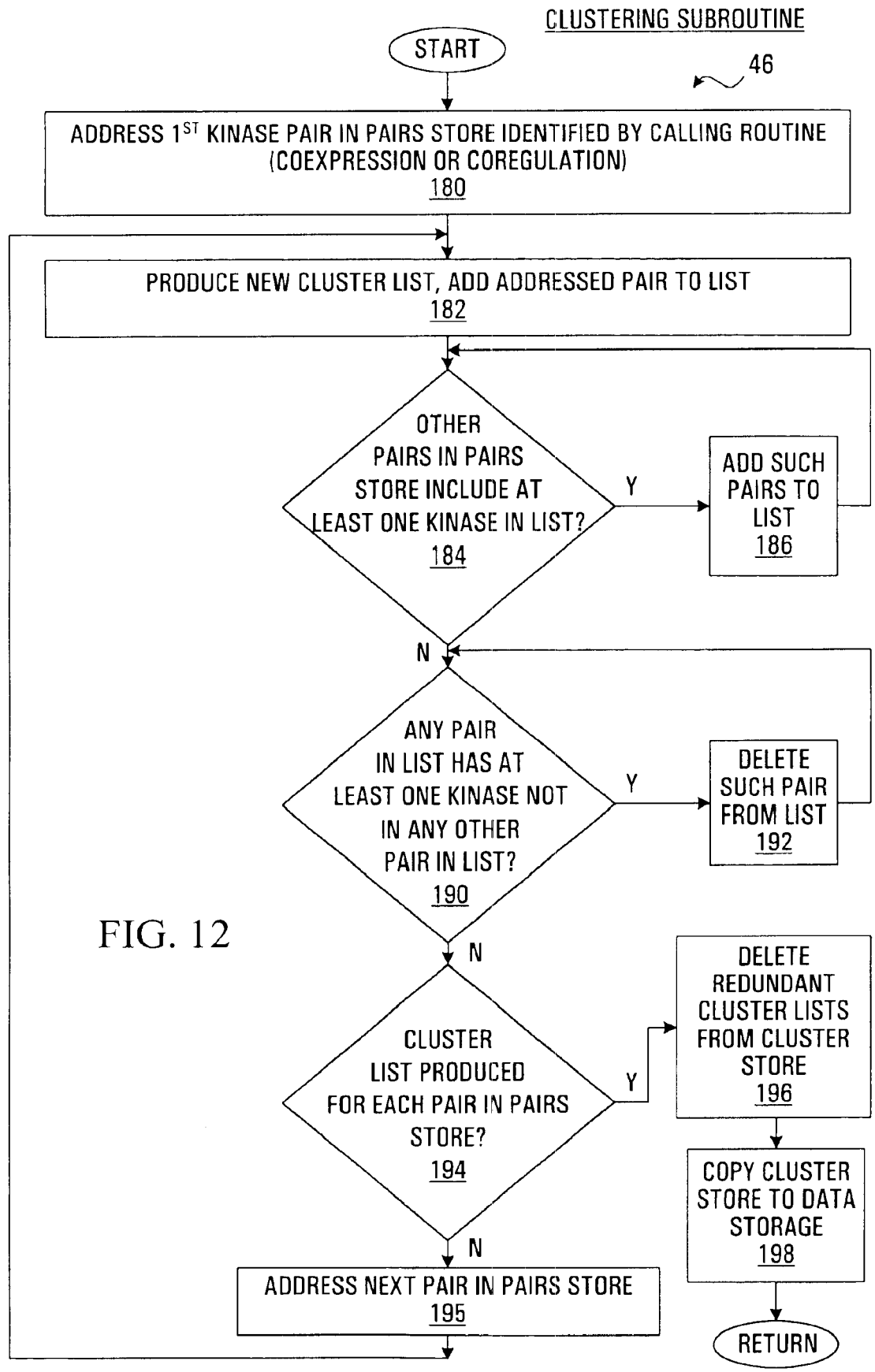
FIG. 12 is a flowchart of a clustering subroutine executed by the processor circuit shown in FIG. 2.

Referring to FIGS. 2, 11 and 12, the clustering subroutine 46 configures the processor circuit to produce a list of clusters of associated cell signaling proteins. More particularly, the clustering subroutine configures the processor circuit to identify a cluster of associated cell signaling proteins, the cluster comprising a group of the pairs of associated cell signaling proteins for which each member of each pair is present in at least one other pair of the group.

The clustering subroutine 46 may be called by either the coexpression routine 40, or the coregulation routine 42, or both. The calling routine stores appropriate pointers in the clustering pointers register 51 in the RAM 20, to provide the clustering subroutine 46 with a pointer to an input area of the RAM 20 where input data for the clustering subroutine is located, and a pointer to an output area of the RAM 20 to which the clustering subroutine is to write its output. For example, when the calling routine is the coexpression routine 40, the clustering pointers register 51 will contain an input pointer to the coexpressed pairs store 64 and an output pointer to the coexpressed clusters store 66. In this example, therefore, the clustering subroutine configures the processor circuit to produce a list of clusters of coexpressed cell signaling protein pairs, each cluster including a group of the pairs of coexpressed cell signaling proteins for which each member of each pair is present in at least one other pair of the group.

The clustering subroutine begins with a first block of codes 180, which directs the processor circuit 16 to address a first cell signaling protein pair in a pairs store (in this example, the coexpressed pairs store 64) identified by the contents of the clustering pointers register 51.

Block 182 then configures the processor circuit to generate a new cluster list associated with the currently addressed cell signaling protein pair, the cluster list including an identification of the addressed cell signaling protein pair.

Block 182 further directs the processor circuit to store the new cluster list in an output area identified by a pointer in the clustering pointers register 51, which in this example is the coexpressed clusters store 66.

Blocks 184 and 186 then effectively configure the processor circuit 16 to add, to the new cluster list, an identification of each of the cell signaling protein pairs in the input area, which in this example is the coexpressed pairs store 64, that includes at least one cell signaling protein already present in the cluster list. Block 184 directs the processor circuit to determine whether any such pairs exist. If so, block 186 directs the processor circuit to add identifications of such pairs to the new cluster list. Block 186 then directs the processor circuit back to block 184 to determine whether the input area contains any cell signaling protein pairs that include at least one cell signaling protein already present in the revised cluster list. In effect, therefore, blocks 184 and 186 configure the processor circuit to repeat the adding following each adding of pairs to the cluster list, to effectively add to the cluster list each of the pairs that includes at least one cell signaling protein present in at least one pair added to the cluster list. Processing continues through blocks 184 and 186 in this manner until no such further pairs exist.

For example, referring to FIGS. 10, 11 and 12, if the currently addressed cell signaling protein pair consists of the kinases A+B, then following block 182, a new cluster list will include only an identification of the pair A+B. Following an initial execution of blocks 184 and 186, the new cluster list 188 will further include identifications of any pairs in the coexpressed pairs store 64 that include either A or B, or in other words, the cluster list 188 will consist of the pairs A+B, A+C, A+D, B+C, B+D and B+E. Following a second execution of blocks 184 and 186, the new cluster list will further include identifications of any pairs that include either C, D or E, or in other words, the new cluster list 188 will consist of A+B, A+C, A+D, B+C, B+D, B+E, C+D and E+F. Upon a third execution of block 184, no further pairs will be located and the processor will be directed to block 190.

Blocks 190 and 192 then configure the processor circuit to eliminate from the new cluster list, each of the pairs that includes at least one cell signaling protein not found in at least one other pair in the cluster list. Block 190 directs the processor circuit to determine whether any such pairs exist, and if so, block 192 directs the processor circuit to eliminate such pairs from the new cluster list and to return to block 190 to determine whether any such pairs exist in respect of the revised list. In effect, therefore, blocks 190 and 192 configure the processor circuit to repeat the eliminating following each eliminating of pairs, to effectively eliminate from the cluster list each of the pairs that includes at least one cell signaling protein not present in at least one other non-eliminated pair in the cluster list.

For example, a first execution of blocks 190 and 192 upon the cluster list 188 consisting of A+B, A+C, A+D, B+C, B+D, B+E, C+D and E+F, will result in the elimination of E+F from the new cluster list, as F is not found in at least one other pair in the cluster list 188. A second execution of blocks 190 and 192 upon the revised list will result in the further elimination of B+E, as E is no longer found in at least one other non-eliminated pair in the cluster list 188. Upon a further execution of block 190, no such pairs will be found, leaving a revised cluster list 188 consisting of A+B, A+C, A+D, B+C, B+D and C+D.

Following the final execution of block 190, block 194 then directs the processor circuit to determine whether a cluster list such as the cluster list 188 has been produced for each cell signaling protein pair in the input area, which in this example is the coexpressed pairs store 64. If not, block 195 directs the processor circuit to address the next cell signaling protein pair in the coexpressed pairs store 64 and the processor is directed back to block 182, to generate a new cluster list corresponding to the newly-addressed cell signaling protein pair.

If at block 194, the processor circuit determines that a cluster list has been produced for each cell signaling protein pair, block 196 then directs the processor circuit to compare the various cluster lists 188 stored in the output area, which in this example is the coexpressed clusters store 66, to each other, to determine whether any of the cluster lists 188 are identical to each other. For example, it will be appreciated that in the exemplary cluster lists illustrated in FIG. 11, a cluster list corresponding to C+D will consist of the same cluster list 188 as that corresponding to A+B. Block 196 therefore directs the processor circuit to delete any such redundant copies of cluster lists from the output area (in this example the coexpressed clusters store 66), so that each cluster appears only once as a combination of pairs, rather than multiple times as a permutation of pairs.

Block 198 then directs the processor circuit to store, in the data storage area 110 of the storage medium 22, a copy of the output area, i.e. a copy of the coexpressed clusters store 66.

Following execution of block 198, the processor circuit 16 is directed to return to whichever routine called the clustering subroutine 46.

Coregulation Routine

Referring to FIGS. 2 and 13–7, the coregulation routine is shown generally at 42 in FIG. 13. Generally, the coregulation routine 42 configures the processor circuit 16 to produce and store, in the memory 18, a comparison value for each pair of the cell signaling proteins in response to the received cell signaling protein data values, and to identify cell signaling protein pairs having comparison values satisfying a condition indicative of an association between the cell signaling proteins. More particularly, the coregulation routine configures the processor circuit to produce, as the comparison values, a coregulation coefficient for each pair of the cell signaling proteins, each coregulation coefficient representing a degree of coregulation of one cell signaling protein of the pair and the other cell signaling protein of the pair.

Referring to FIGS. 2, 4, 13 and 14, the coregulation routine 42 begins with a first block of codes 200, which directs the processor circuit 16 to generate state data corresponding to the contents of the input data values store 54, and to store such state data in the state data store 61. Block 200 directs the processor circuit to sequentially address each cell signaling protein data record 112 in the input data values store 54, and for each addressed cell signaling protein data record, the processor circuit is directed to sequentially address each of the ten data sets 202 of the input data values store 54.

Block 200 further directs the processor circuit to read the contents of the phosphorylated measurement field 124 and the dephosphorylated measurement field 126 corresponding to the currently addressed data set 202 and the currently addressed cell signaling protein data record 112. If the contents of the phosphorylated measurement field 124 are greater than or equal to both the contents of the dephosphorylated measurement field 126 and a predetermined value, which in this embodiment is 20, then block 200 directs the processor circuit to store an indication of a phosphorylated state, such as an active bit or a "P" for example, in a state data field 204 of a cell signaling protein state record 206 in the state data store 61, corresponding to the currently addressed cell signaling protein data record 112 and data set 202. Conversely, if the contents of the dephosphorylated measurement field 126 are greater than the contents of the phosphorylated measurement field 124 and are greater than or equal to the predetermined value, then an indication of a dephosphorylated state, such as an inactive bit or a "D" for example, is stored in the corresponding state data field 204 of the cell signaling protein state record 206. If the contents of the phosphorylated measurement field 124 and the dephosphorylated measurement field 126 are both less than the predetermined value, then block 200 directs the processor circuit to store in the state data field 204 an indication that no reliable conclusion as to the phosphorylation state of the cell signaling protein may be drawn for this particular data set, such as a string "NS" representing "No Signal", for example.

Alternatively, rather than merely distinguishing between phosphorylated and dephosphorylated states in a binary manner, for some applications it may be desirable to distinguish between partial degrees of phosphorylation. For example, it may be desirable to assign an indication "D" representing a dephosphorylated state when the amount of the cell signaling protein detected in the dephosphorylated state, expressed as a percentage $X_D$ of the total detected amount of the cell signaling protein, falls in the range $90\% \leq X_D \leq 100\%$, to assign an indication P1 of a first phosphorylated state when $60\% \leq X_D < 90\%$, to assign an indication P2 of a second phosphorylated state when $30\% \leq X_D < 60\%$, and to assign an indication P3 of a third phosphorylated state when $0\% \leq X_D < 30\%$.

In this embodiment, block 200 directs the processor to continue producing and storing two-state (P or D) phosphorylation state data, until a cell signaling protein state record 206 has been produced and stored for all cell signaling proteins, each state record including a state data field 204 for each of the ten data sets.

Referring to FIGS. 2, 13 and 14, block 208 then directs the processor circuit 16 to address the cell signaling protein state records 206 corresponding to a first cell signaling protein pair, such as an exemplary cell signaling protein pair 210 shown in FIG. 14, consisting of the kinases A and B.

Block 212 then configures the processor circuit to assign, for each of the ten data sets, a pair state value, as a function of phosphorylation states of one cell signaling protein and the other cell signaling protein of the currently addressed cell signaling protein pair. Any suitable function may be used, but preferably, the selection of the function for producing the pair state values reflects the following three principles. If both members of a particular pair of kinases or other cell signaling proteins are consistently found in a phosphorylated state, this is strongly suggestive of a coregulation association between the kinases. If both members of the pair are consistently found in a dephosphorylated state, this still suggests a coregulation association, but may alternatively be explained by the coincidental fact that in most situations, the majority of kinases are in dephosphorylated states, and therefore, the likelihood of coregulation is not as high as if they were both found to be phosphorylated. Conversely, if both members of the pair are frequently found in opposite phosphorylation states, this strongly suggests that the members are not coregulated.

Thus, in this embodiment, to reflect these three principles, block 212 configures the processor circuit 16 to assign such pair state values by assigning a first pair state value when the one cell signaling protein and the other cell signaling protein of the pair are both in a phosphorylated state, by assigning a second pair state value when the one cell signaling protein and the other cell signaling protein are both in a dephosphorylated state, the second pair state value being less than the first pair state value, and by assigning a third pair state value when the one cell signaling protein and the other cell signaling protein are in different phosphorylaton states, the third pair state value being less than the second pair state value. More particularly, in this embodiment the first pair state value is +3, the second pair state value is +1, and the third pair state value is −3. If, for any of the ten data sets 214, the state data field 204 of the cell signaling protein state record 206 of either of the cell signaling proteins of the currently addressed pair contains a value indicative of an unreliable phosphorylation state determination, such as "N.S." for example, block 212 directs the processor circuit to omit producing any pair state value for that particular data set 214 for the currently addressed pair. Block 212 directs the processor circuit to temporarily store the pair state values produced for the currently addressed cell signaling protein pair, in a pair state calculation area (not shown) in the program store 50 in the RAM 20.

Block 216 then configures the processor circuit 16 to produce and store a coregulation coefficient corresponding to the one cell signaling protein and the other cell signaling protein of the currently addressed cell signaling protein pair. Block 216 first directs the processor circuit to add the pair state values for each of the sets, as produced at block 212, to produce a sum of pair state values corresponding to the currently addressed cell signaling protein pair. Block 216 further configures the processor circuit to divide the sum by the number of sets, to produce the coregulation coefficient corresponding to the one cell signaling protein and the other cell signaling protein. This division is a division by the number of sets for which pair state values were actually produced for the pair, which may differ from the total number of data sets if any of the state data fields 204 contained "N.S." indicating unreliable phosphorylation state data. If the coregulation coefficient is negative, in this embodiment block 216 directs the processor circuit to set the coregulation coefficient equal to zero. Alternatively, however, such coregulation coefficients may be left as negative values if desired.

Referring to FIGS. 13 and 15, block 216 further directs the processor circuit to store the coregulation coefficient in the coregulation coefficients store 68, or more particularly, in a coregulation coefficient field 218 of a cell signaling protein coregulation record 220 corresponding to the first cell signaling protein of the currently addressed pair 210. As shown in FIG. 15, each cell signaling protein coregulation record 220 includes a cell signaling protein identification field 222, and further includes a plurality of coregulation coefficient fields 218, containing a plurality of respective coregulation coefficients corresponding to the coregulation of the cell signaling protein identified in the identification field 222 and every other successive cell signaling protein (e.g. every kinase whose corresponding coregulation record 220 appears beneath the current coregulation record 220 in the coregulation coefficients store 68 shown in FIG. 15). It will be appreciated that for the purpose of analyzing coregulation, it is unnecessary to treat the cell signaling protein pairs as permutations rather than combinations, as the coregulation of cell signaling protein B with cell signaling protein A for example is necessarily identical to the coregulation of A with B. However, if desired, each coregulation record 220 may redundantly contain coregulation coefficients for the identified cell signaling protein and all other cell signaling proteins, rather than merely successive proteins.

Block 224 then directs the processor circuit 16 to determine whether pair state values and coregulation coefficients have been produced for all possible cell signaling protein pairs, and if not, block 226 directs the processor circuit to address the cell signaling protein state records 206 in the state data store 61 corresponding to the next cell signaling protein pair, and to return to block 212 to continue assigning pair state values and producing coregulation coefficients, as described above.

Referring to FIGS. 13, 15 and 16, if at block 224, coregulation coefficients have been produced for all cell signaling protein pairs, block 228 configures the processor circuit 16 to identify cell signaling protein pairs having comparison values satisfying a condition indicative of an association between the cell signaling proteins, and to produce a list of such pairs of associated cell signaling proteins. More particularly, block 228 configures the processor circuit to identify and produce a list of coregulated cell signaling protein pairs, the list including an identification of each cell signaling protein pair having a coregulation coefficient greater than a threshold coregulation value. In this embodiment, the threshold coregulation value is zero, so that any pairs having coregulation coefficients that are negative or equal to zero will be omitted from the list. Alternatively, other threshold values may be substituted. Block 228 further directs the processor circuit to store the list of coregulated pairs so identified in the coregulated pairs store 70 in the RAM 20, as shown at 70 in FIG. 16. In addition, block 228 directs the processor circuit to store copies of the coregulation coefficients store 68 and the coregulated pairs store 70 in the storage area 110 of the storage medium 22, to enable subsequent retrieval if desired.

Referring to FIGS. 2 and 13, block 230 then directs the processor circuit 16 to call the clustering subroutine 46, to produce a list of clusters of coregulated cell signaling protein pairs, each cluster including a group of the coregulated cell signaling protein pairs for which each member of each pair is present in at least one other pair of the group. Block 230 further directs the processor circuit to store, in the clustering pointers register 51, an input area pointer identifying the coregulated pairs store 70 as the location of input data for the clustering subroutine, and an output area pointer identifying the coregulated clusters store 72 as the location to which the clustering subroutine is to write its output.

Referring to FIGS. 2, 12, 16 and 17, the clustering subroutine 46 then directs the processor circuit 16 to analyze the contents of the coregulated pairs store shown at 70 in FIG. 16, and to produce and store, as the contents of the coregulated clusters store 72 shown in FIG. 17, a list of clusters of coregulated cell signaling protein pairs, each cluster including a group of coregulated cell signaling protein pairs for which each member of each pair is present in at least one other pair of the group. The production of such a coregulated clusters list proceeds in precisely the same manner as described above in connection with the production of the contents of the coexpressed clusters store 66, and is therefore not described in further detail.

Block 232 then directs the processor circuit 16 to output the contents of the coregulated pairs store 70 and the coregulated clusters store 72. As with the output of coexpressed pairs and clusters, such output may include generating a printout or a display, or writing to a computer-readable medium, or transmitting the output to a remote device, for example.

It will be appreciated that the output contents of the coregulated pairs store 70 and the coregulated clusters store 72 shown in FIGS. 16 and 17 respectively, suggest the following conclusions. Kinases A, B, C, D, E, F, G and H are commonly coregulated and may operate in common signaling pathways. Kinases I, J, K, L, M, N, O and P are commonly coregulated and may operate in common signaling pathways. Similarly, kinases Q, R, S and T are commonly coregulated and may operate in common signaling pathways.

The coregulation routine 42 is then ended.

Linkage Routine

Figure 18:
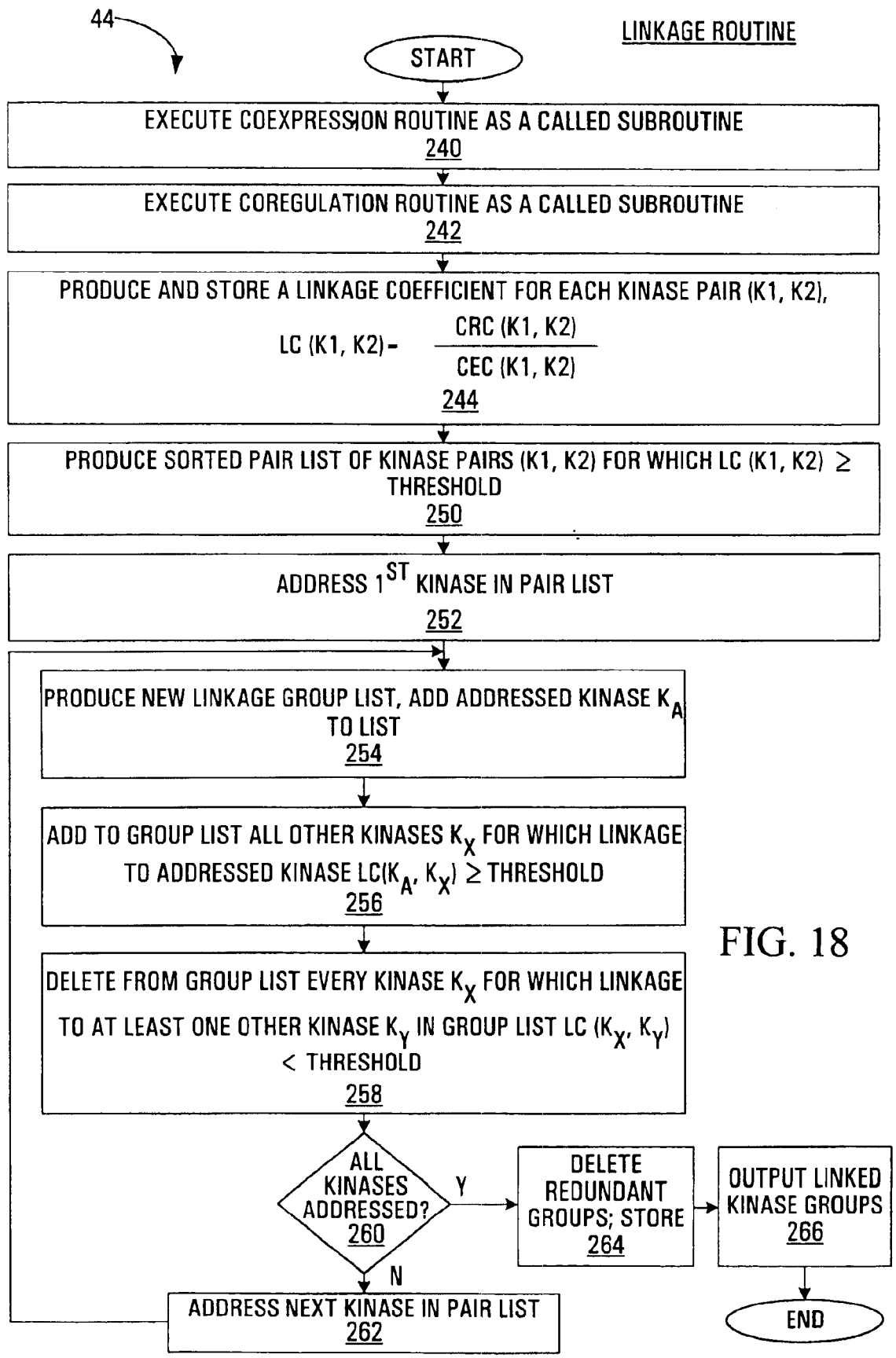
FIG. 18 is a flowchart of a linkage routine executed by the processor circuit shown in FIG. 2.

Referring to FIG. 18, the linkage routine is shown generally at 44. Generally, the linkage routine 44 configures the processor circuit 16 to produce and store, in the memory 18, a comparison value for each pair of cell signaling proteins in response to the received data values, and to identify cell signaling protein pairs having comparison values satisfying a condition indicative of an association between the cell signaling proteins. More particularly, in this embodiment the linkage routine configures the processor circuit to produce, as the comparison values, a linkage coefficient for each pair of the cell signaling proteins, as a function of a coexpression coefficient representing a degree of coexpression of one cell signaling protein of the pair and the other cell signaling protein of the pair, and of a coregulation coefficient representing a degree of coregulation of the one cell signaling protein of the pair and the other cell signaling protein of the pair, each linkage coefficient representing a degree of association between the one cell signaling protein and the other cell signaling protein.

Referring back to FIG. 3, it will be recalled that the linkage routine is invoked either in response to an express user request detected at block 139 of the receive data routine 36, or alternatively, is invoked as a default in the absence of any routine selection by the user.

Accordingly, referring to FIGS. 2 and 18, the linkage routine 44 begins with a first block of codes 240 which directs the processor circuit 16 to execute the coexpression routine 40 as a called subroutine, in order to produce and store the contents of the coexpressed pairs store 64 and the coexpressed clusters store 66 as discussed above. Similarly, block 242 directs the processor circuit to execute the coregulation routine 42 as a called subroutine, in order to produce and store the contents of the coregulated pairs store 70 and the coregulated clusters store 72 as discussed above.

Referring to FIGS. 2, 9, 15, 18 and 19, block 244 then configures the processor circuit 16 to produce each linkage coefficient by, for each pair, dividing the coregulation coefficient by the coexpression coefficient. More particularly, for each pair of cell signaling proteins, block 244 directs the processor to read the contents of the coregulation coefficient field 218 in the coregulation coefficients store 68 corresponding to the pair, and to divide such contents by the contents of the coexpression coefficient field 162 in the coexpression coefficient store 62 corresponding to the pair. For the purpose of such division, if the contents of the coexpression coefficient field 162 are zero, block 244 directs the processor circuit to instead divide the coregulation coefficient by an arbitrary small number, such as $1 \times 10^{-4}$ for example, to avoid division-by-zero errors.

Referring to FIGS. 18 and 19, block 244 further directs the processor circuit to multiply the result of the above division by 100 to produce the linkage coefficient, and to store the linkage coefficient in the linkage coefficients store 74, or more particularly, in a linkage coefficient field 246 of a cell signaling protein linkage record 248 corresponding to the first cell signaling protein of the corresponding pair of cell signaling proteins. As shown in FIG. 19, each cell signaling protein linkage record 248 includes a cell signaling protein identification field 249, and further includes a plurality of linkage coefficient fields 246, containing a plurality of respective linkage coefficients corresponding to the linkage of the cell signaling protein identified in the identification field 249 and every other successive cell signaling protein (e.g. every kinase whose corresponding linkage record 248 appears beneath the current linkage record 248 in the linkage coefficients store 74 shown in FIG. 19). It will be appreciated that for the purpose of analyzing linkage, it is unnecessary to treat the cell signaling protein pairs as permutations rather than combinations, as the linkage of B with A for example is necessarily identical to the linkage of A with B. However, if desired, each linkage record 248 may redundantly contain linkage coefficients for the identified cell signaling protein and all other cell signaling proteins, rather than merely for successive cell signaling proteins. In examining the contents of the linkage coefficients store 74, it will be appreciated that a disproportionately large number of "zero" linkage coefficients are present, as a result of the decision at block 216 of the coregulation routine 42 to universally set negative coregulation coefficients equal to zero, as discussed above.

When all such linkage coefficients have been produced and stored in the linkage coefficients store 74, block 244 further directs the processor circuit to copy the linkage coefficients store 74 to the data storage area 110 of the storage medium 22, for future retrieval if desired.

Referring to FIGS. 2, 18 and 20, block 250 then configures the processor circuit to produce a list of linked cell signaling protein pairs, the list including an identification of each cell signaling protein pair having a linkage coefficient greater than or equal to a threshold linkage value. In this embodiment, the threshold linkage value is 0.5, however, other threshold values may be substituted. Block 250 further directs the processor circuit to sort the list of such linked cell signaling protein pairs by linkage coefficient in descending order, and to store the sorted list as the contents of the linkage-sorted pairs store 76 shown in FIG. 20. A copy of the linkage-sorted pairs store 76 is then copied to the data storage area 110 of the storage medium 22.

Blocks 252 to 262 then configure the processor circuit 16 to associate at least some of the cell signaling proteins with respective common signaling pathways, in response to the linkage coefficients. More particularly, blocks 252 to 262 configure the processor circuit to associate the cell signaling proteins with the pathways by identifying a group of the cell signaling proteins for which each linkage coefficient linking each cell signaling protein to each other cell signaling protein of the group is greater than or equal to a threshold linkage value. In this manner, the processor circuit is configured to produce lists of the common signaling pathways.

Block 252 first directs the processor circuit to address a first individual cell signaling protein present in at least one pair in the linkage-sorted pairs store 76.

Block 254 then configures the processor circuit 16 to generate a linkage list including an identification of the currently addressed cell signaling protein. Block 254 further directs the processor circuit to store the newly-generated linkage list in the linked pathway groups store 78.

Block 256 configures the processor circuit 16 to add to the new linkage list, an identification of each other cell signaling protein for which the linkage coefficient for the currently addressed cell signaling protein and the other cell signaling protein is greater than or equal to the threshold linkage value. For example, referring to FIGS. 18, 19 and 21, if the currently addressed cell signaling protein is kinase C, then a new linkage list 257 corresponding to kinase C will temporarily consist of kinases A, B, C, D, G and H.

Block 258 then configures the processor circuit to eliminate, from the linkage list, each cell signaling protein on the linkage list for which the linkage coefficient for that cell signaling protein and at least one other cell signaling protein on the linkage list is less than the threshold linkage value. Continuing the previous example wherein the currently addressed cell signaling protein is kinase C, block 258 will direct the processor circuit to eliminate kinases A and B from the linkage list 257, because each of A and B has a linkage coefficient less than the threshold linkage value for at least one other kinase in the linkage list (such as G for example), leaving only kinases C, D, G and H remaining in the new linkage list 257 stored in the linked pathway groups store 78.

In effect, therefore, blocks 252 to 258 serve to produce a linked group of cell signaling proteins, for which every member of the group has a linkage coefficient with every other member of the group greater than or equal to the threshold linkage value.

Block 260 directs the processor circuit to determine whether all of the cell signaling proteins in the linkage-sorted pairs store 76 have been addressed to produce respective linked pathway groups in this manner. If not, block 262 directs the processor circuit to address the next such cell signaling protein, and the processor circuit is directed back to block 254 to produce a new linkage list corresponding to the newly addressed cell signaling protein, and to store the new linkage list in the linked pathway groups store 78.

If at block 260, linkage lists representing respective linked pathway groups have been produced for all cell signaling proteins, block 264 directs the processor circuit 16 to compare the various linkage lists stored in the linked pathway groups store 78 to each other, and to delete any redundant duplicate linkage lists that may exist therein. Block 264 then directs the processor circuit to copy the linked pathway groups store 78 to the data storage area 110 of the storage medium 22, for future retrieval if desired.

Block 266 then directs the processor circuit to output the contents of the linkage-sorted pairs store 76 and the linked pathway groups store 78. The output of the contents of the linked pathway groups store 78 directly represents groups of cell signaling proteins forming respective common signaling pathways, such as the six signaling pathway groups of kinases shown in FIG. 21. As with the coexpression and coregulation outputs discussed above, such outputs may include printouts, recordings on media, transmissions, or other forms of output.

The linkage routine 44 is then ended.

Further Measurements

Once a number of common signaling pathways have been identified, such as the groups listed in the linked pathway groups store 78 for example, the next desirable step is to determine the "order" of the cell signaling proteins within each signaling pathway. Only limited inferences in this regard may be drawn from the foregoing linkage coefficient analysis.

However, by performing additional time course studies, in which the phosphorylation states of cell signaling proteins such as kinases and their substrates are carefully monitored at various times immediately after the exposure of a cell to different stimuli, it may be possible to determine the order of the cell signaling proteins within each signaling pathway. For example, in each data set, a time after the introduction of a stimulus at which a given kinase has experienced a 50% of maximal change in phosphorylation may be recorded, and the average such time over all data sets may be calculated. Such average phosphorylation change times may then be employed to determine a signaling order within a given signaling pathway. It may then be possible to derive a suitable set of rules for determining, for example, whether a given upstream kinase within a signaling pathway is triggering two subsequent downstream kinases in series or in parallel.

While specific embodiments of the invention have been described and illustrated, such embodiments should be considered illustrative of the invention only and not as limiting the invention as construed in accordance with the accompanying claims.

What is claimed is:

1. A method of identifying associated cell signaling proteins, the method comprising:
   a) producing and storing a comparison value for each pair of said cell signaling proteins in response to data values representing physical properties of respective cell signaling proteins; and
   b) identifying cell signaling protein pairs having comparison values satisfying a condition indicative of an association between the cell signaling proteins,
      wherein producing a comparison value comprises producing a linkage coefficient for each pair of said cell signaling proteins, as a function of a coexpression coefficient representing a degree of coexpression of one cell signaling protein of said pair and the other cell signaling protein of said pair, and of a coregulation coefficient representing a degree of coregulation of said one cell signaling protein of said pair and said other cell signaling protein of said pair, each said linkage coefficient representing a degree of association between said one cell signaling protein and said other cell signaling protein, and wherein, producing said linkage coefficient comprises, for each said pair, dividing said coregulation coefficient by said coexpression coefficient.

2. The method of claim 1 wherein producing and storing comprises producing and storing in a random access memory, said comparison value.

3. The method of claim 1 further comprising normalizing said data values relative to at least one reference value, prior to producing said comparison values.

4. The method of claim 1 wherein identifying comprises producing a list of pairs of associated cell signaling proteins.

5. The method of claim 1 wherein identifying comprises producing a list of clusters of associated cell signaling proteins.

6. The method of claim 4 wherein identifying further comprises identifying a cluster of associated cell signaling proteins, said cluster comprising a group of said pairs of associated cell signaling proteins for which each member of each said pair is present in at least one other pair of said group.

7. The method of claim 5 wherein identifying each said cluster comprises:
   a) generating a cluster list associated with a first cell signaling protein pair, said cluster list comprising an identification of said first cell signaling protein pair;
   b) adding, to said cluster list, an identification of each of said pairs that includes at least one cell signaling protein already present in said cluster list;
   c) repeating said adding following each said adding of pairs to said cluster list, to effectively add to said cluster list each of said pairs that includes at least one cell signaling protein present in at least one pair added to said cluster list;
   d) eliminating, from said cluster list, each of said pairs that includes at least one cell signaling protein not found in at least one other pair in said cluster list; and
   e) repeating said eliminating following each said eliminating of pairs, to effectively eliminate from said cluster list each of said pairs that includes at least one cell signaling protein not present in at least one other non-eliminated pair in said cluster list.

8. The method of claim 1 further comprising receiving sets of cell signaling protein data, each set comprising data values representing amounts of respective corresponding cell signaling proteins in biological material corresponding to said set, wherein producing each said coexpression coefficient comprises:
   a) for each set of data values representing amounts of respective corresponding cell signaling proteins in biological material, calculating a difference value equal to an absolute value of a difference between said data value corresponding to said one cell signaling protein and said data value corresponding to said other cell signaling protein; and
   b) adding said difference values for each of said sets to produce a sum of difference values.

9. The method of claim 8 wherein producing each said coexpression coefficient further comprises dividing said sum by the number of said sets to produce said coexpression coefficient corresponding to said one cell signaling protein and said other cell signaling protein.

10. The method of claim 1 further comprising receiving sets of cell signaling protein data, each set comprising data values indicating phosphorylation states of respective cell signaling proteins in biological material corresponding to said set, wherein producing each said coregulation coefficient comprises:
   a) for each set of data values indicating phosphorylation states of respective cell signaling proteins in biological material, assigning a pair state value as a function of phosphorylation states of said one cell signaling protein and said other cell signaling protein; and
   b) adding said pair state values for each of said sets to produce a sum of pair state values.

11. The method of claim 10 wherein assigning a pair state value comprises:
   a) assigning a first pair state value when said one cell signaling protein and said other cell signaling protein are both in a phosphorylated state,
   b) assigning a second pair state value when said one cell signaling protein and said other cell signaling protein are both in a dephosphorylated state, said second pair state value being less than said first pair state value; and
   c) assigning a third pair state value when said one cell signaling protein and said other cell signaling protein are in different phosphorylation states, said third pair state value being less than said second pair state value.

12. The method of claim 1 further comprising associating at least some of said cell signaling proteins with respective common signaling pathways, in response to said linkage coefficients.

13. The method of claim 12 wherein associating comprises identifying a group of said cell signaling proteins for which each said linkage coefficient linking each cell signaling protein to each other cell signaling protein of said group is greater than or equal to a threshold linkage value.

14. The method of claim 13 wherein identifying said group comprises:
   a) generating a linkage list comprising a first cell signaling protein;
   b) adding, to said linkage list, each other said cell signaling protein for which said linkage coefficient for said first cell signaling protein and said other cell signaling protein is grather than or equal to said threshold linkage value; and
   c) eliminating, for said linkage list, each cell signaling protein on said linkage list for which said linkage coefficient for said each cell signaling protein and at least one other cell signaling protein on said linkage list is less than said threshold linkage value.

15. The method of claim 14 further comprising producing lists of said common signaling pathways.

* * * * *